United States Patent [19]
Butler et al.

[11] Patent Number: 5,097,045

[45] Date of Patent: Mar. 17, 1992

[54] PROCESS FOR TRANS-6-[2-(SUBSTITUTED-PYRROL-1-YL)ALKYL]PYRAN-2-ONE INHIBITORS OF CHOLESTEROL SYNTHESIS

[75] Inventors: Donald E. Butler; Carl F. Deering; Alan Millar; Thomas N. Nanninga, all of Holland; Bruce D. Roth, Ann Arbor, all of Mich.

[73] Assignee: Warner-Lambert Company, Morris Plains, N.J.

[21] Appl. No.: 595,461

[22] Filed: Oct. 9, 1990

Related U.S. Application Data

[60] Division of Ser. No. 303,733, Feb. 1, 1989, Pat. No. 5,003,080, which is a continuation-in-part of Ser. No. 158,439, Feb. 22, 1988, abandoned.

[51] Int. Cl.$^5$ ............................................. C07D 319/06
[52] U.S. Cl. ................................. 549/373; 548/407; 548/517; 548/537; 549/333; 564/169
[58] Field of Search ............................... 549/333, 373

[56] References Cited

U.S. PATENT DOCUMENTS

| | | | |
|---|---|---|---|
| 4,320,024 | 3/1982 | Reierson et al. | 549/373 |
| 4,647,576 | 3/1987 | Hoefle et al. | 514/422 |
| 4,681,893 | 7/1987 | Roth | 514/422 |

FOREIGN PATENT DOCUMENTS

| | | | |
|---|---|---|---|
| 0759519 | 8/1980 | U.S.S.R. | 549/373 |

Primary Examiner—Joseph Paul Brust
Attorney, Agent, or Firm—Francis J. Tinney

[57] ABSTRACT

An improved process for the preparation of trans-6-[2-(substituted-pyrrol-1-yl)alkyl]pyran-2-ones by a novel synthesis is described where 1,6-heptadien-4-ol is converted in eight operations to the desired products, as well as an improved process for the preparation of (2R-trans) and trans-(±)-5-(4-fluorophenyl)-2-(1-methylethyl)-N,4-diphenyl-1-[2-(tetrahydro-4-hydroxy-6-oxo-2H-pyran-2-yl)ethyl]1H-pyrrole-3-carboxamide by a novel synthesis where 4-methyl-3-oxo-N-phenylpentanamide is converted in eight operations to the desired product or alternatively 4-fluoro-α-[2-methyl-1-oxopropyl]-γ-oxo-N,β-diphenylbenzenebutaneamide is converted in one step to the desired product, and additionally, a process for preparing (2R-trans)-5-(4-fluorophenyl)-2-(1-methylethyl)-N,4-diphenyl-1-[2-(tetrahydro-4-hydroxy-6-oxo-2H-pyran-2-yl)ethyl]-1H-pyrrole-3-carboxamide from (R)-4-cyano-3-[[(1,1-dimethylethyl)dimethylsilyl]oxy]butanoic acid, as well as other valuable intermediates used in the processes.

9 Claims, No Drawings

PROCESS FOR TRANS-6-[2-(SUBSTITUTED-PYRROL-1-YL)ALKYL]PYRAN-2-ONE INHIBITORS OF CHOLESTEROL SYNTHESIS

This is a divisional application of U.S. Ser. No. 07/303,733, filed Feb. 1, 1989, now U.S. Pat. No. 5,003,080 which is a continuation-in-part application of U.S. Ser. No. 07/158,439, filed in Feb. 22, 1988, now abandoned.

BACKGROUND OF THE INVENTION

U.S. Pat. No. 4,647,576, which is herein incorporated by reference, discloses certain trans-6-[2-(substituted-pyrrol-1-yl)alkyl]-pyran-2-ones.

U.S. Pat. No. 4,681,893, which is herein incorporated by reference, discloses certain trans-6-[2-(3- or 4-carboxamido-substituted pyrrol-1-yl)alkyl]-4-hydroxypyran-2-ones.

The compounds disclosed in the above United States patents are useful as inhibitors of the enzyme 3-hydroxy-3-methylglutaryl-coenzyme A reductase (HMG-CoA reductase) and are thus useful hypolipidemic and hypocholesterolemic agents. Particularly valuable as hypolipidemic and hypocholesterolemic agents are trans($\pm$) 5-(4-fluorophenyl)-2-(1-methylethyl)-N,4-diphenyl-1-[2-(tetrahydro-4-hydroxy-6-oxo-2H-pyran-2-yl)ethyl]-1H-pyrrole-3-carboxamide and (2R-trans)-5-(4-fluorophenyl)-2-(1-methylethyl)-N,4-diphenyl-1-[2-(tetrahydro-4-hydroxy-6-oxo-2H-pyran-2-yl)ethyl]-1H-pyrrole-3-carboxamide. The aforementioned compounds have been prepared by a linear synthetic route which employed two reactions conducted at low temperatures ($-78°$ C.) under carefully controlled conditions. The two reactions included the addition of the dianion of ethyl acetoacetate to an aldehyde and the reduction of the hydroxy ketone produced in this reaction with sodium borohydride and a trialkylborane. Although these reactions provide the target compounds in high diastereomeric excess, they are difficult to conduct on large-scale and use expensive reagents which are difficult to handle. They also do not produce enantiomerically pure products. The materials produced by the earlier methods can be separated into enantiomerically pure products but the process is very expensive, time-consuming, and results in the loss of more than 50% of the starting material.

The object of the present invention is an improved process for preparing the compounds described above by using a novel synthesis.

Further, we have unexpectedly found that the particularly valuable hypolipidemic and hypocholesterolemic agents trans($\pm$)5-(4-fluorophenyl)-2-(1-methylethyl)-N,4-diphenyl-1-[2-(tetrahydro-4-hydroxy-6-oxo-2H-pyran-2-yl)ethyl]-1H-pyrrole-3-carboxamide and (2R-trans)-5-(4-fluorophenyl)-2-(1-methylethyl)-N,4-diphenyl-1-[2-(tetrahydro-4-hydroxy-6-oxo-2H-pyran-2-yl)ethyl]-1H-pyrrole-3-carboxamide can be prepared from a novel intermediate in fewer steps and higher yields than the previous methods. Moreover, the present method proceeds from inexpensive starting materials and is amenable to large-scale synthesis.

SUMMARY OF THE INVENTION

Accordingly, a first aspect of the present invention is an improved process for the preparation of a compound of Formula I

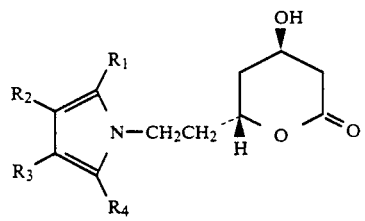

and a dihydroxy acid and pharmaceutically acceptable salts thereof, corresponding to the opened lactone ring of a compound of Formula I wherein $R_1$ is
1-naphthyl,
2-naphthyl,
cyclohexyl,
cyclohexylmethyl,
norbornenyl,
phenyl,
phenyl substituted with
  fluorine,
  chlorine,
  bromine,
  hydroxyl,
  trifluoromethyl,
  alkyl of from one to four carbon atoms,
  alkoxy of from one to four carbon atoms, or
  alkanoyloxy of from two to eight carbon atoms,
benzyl,
2-, 3-, or 4-pyridinyl, or
2-, 3-, or 4-pyridinyl-N-oxide;
$R_2$ or $R_3$ is independently
hydrogen,
alkyl of from one to six carbon atoms,
cyclopropyl,
cyclobutyl,
cyclopentyl,
cyclohexyl,
phenyl,
phenyl substituted with
  fluorine,
  chlorine,
  bromine,
  hydroxyl,
  trifluoromethyl,
  alkyl of from one to four carbon atoms, or
  alkoxy of from one to four carbon atoms,
cyano,
trifluoromethyl, or —$CONR_5R_6$ where $R_5$ and $R_6$ are
  independently
  hydrogen,
  alkyl of from one to six carbon atoms,
  phenyl,
  phenyl substituted with
    fluorine,
    chlorine,
    bromine,
    cyano, or
    trifluoromethyl;
$R_4$ is
alkyl of from one to six carbon atoms,
cyclopropyl,
cyclobutyl,
cyclopentyl,
cyclohexyl, or
trifluoromethyl;
which comprises:

(a) reacting 1,6-heptadien-4-ol with an
 (1) alkyl lithium
 (2) followed by iodine and carbon dioxide and
 (3) treating the resulting iodocarbonate intermediate in situ with a base in an aqueous alcohol at about 0° C. to about 40° C. to afford a compound of Formula IX;

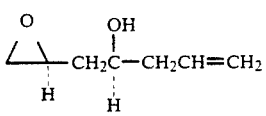

(b) treating the compound of Formula IX with
 (1) an alkali cyanide at about 0° C. to about 40° C. and
 (2) reacting the resulting diol intermediate in situ with a ketal-forming reagent in the presence of an acid to afford a compound of Formula VIII

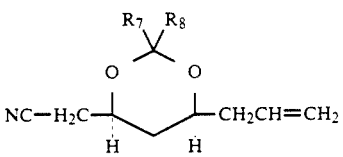

wherein $R_7$ and $R_8$ are independently hydrogen, alkyl of from one to three carbon atoms, phenyl or $R_7$ and $R_8$ taken together as $-(CH_2)_n-$, wherein n is 4 or 5;
 (c) treating the compound of Formula VIII with
 (1) ozone in an inert solvent and
 (2) reacting the resulting intermediate in situ with oxygen and triphenylphosphine at about $-20°$ C. to about $-78°$ C. to afford a compound of Formula VII

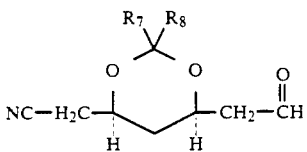

wherein $R_7$ and $R_8$ are as defined above;
 (d) treating the compound of Formula VII with an oxidizing reagent at about 0° C. to afford a compound of Formula VI

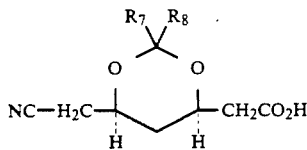

wherein $R_7$ and $R_8$ are as defined above;
 (e) treating the compound of Formula VI with a compound of Formula Hal—$R_{9a}$ wherein Hal is halogen and $R_{9a}$ is alkyl of from one to eight carbon atoms or a three- to six-membered cycloalkyl group, in the presence of a base to afford a compound of Formula $V_a$

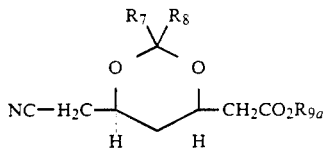

wherein $R_7$, $R_8$, and $R_{9a}$ are as defined above; or treating the compound of Formula VI with a compound of Formula HO—$R_{9b}$ wherein $R_{9b}$ is tertiary butyl, tertiary amyl, or $\alpha$, $\alpha$-dimethylbenzyl in the presence of an activating agent, a catalytic amount of a base and an inert solvent to afford a compound of Formula $V_b$

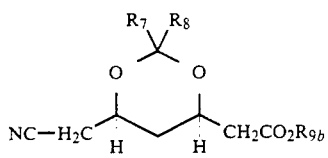

wherein $R_7$, $R_8$, and $R_{9b}$ are as defined above;
 (f) treating the compound of Formula $V_a$ with hydrogen in the presence of a catalyst and an acid at about 0° C. to about 70° C. to afford a compound of Formula $IV_a$

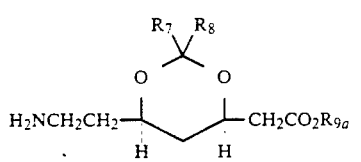

wherein $R_7$, $R_8$, and $R_{9a}$ are as defined above, or treating the compound of Formula $V_b$ with hydrogen in the presence of a catalyst and an acid or a catalyst and a base at about 0° C. to about 70° C. to afford a compound of Formula $IV_b$

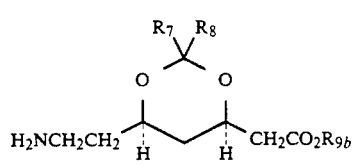

wherein $R_7$, $R_8$, and $R_{9b}$ are as defined above;
 (g) treating the compound of Formula $IV_a$ with a compound of Formula III

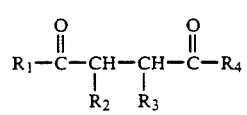

wherein $R_1$, $R_2$, $R_3$, and $R_4$ are as defined above in an inert solvent to afford a compound of formula $II_a$

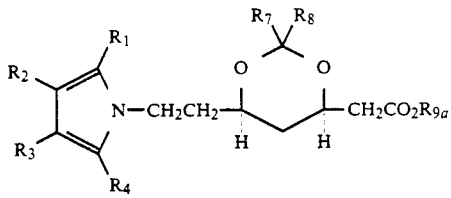

wherein $R_1$, $R_2$, $R_3$, $R_4$, $R_7$, $R_8$, and $R_{9a}$ are as defined above, or treating the compound of formula $IV_b$ with a compound of Formula III in an inert solvent to afford a compound of formula $II_b$

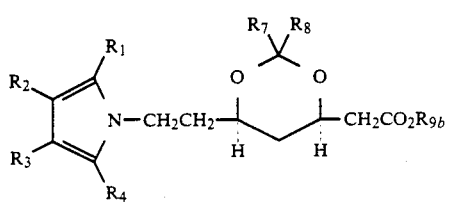

wherein $R_1$, $R_2$, $R_3$, $R_4$, $R_7$, and $R_8$, and $R_{9b}$ are as defined above;

(h) and finally treating a compound of Formula $II_a$ with (1) an acid in the presence of an inert solvent (2) followed by hydrolysis with a base (3) followed by neutralization with an acid and (4) dissolution and/or heating in an inert solvent with concomitant removal of water to give a compound of Formula I, or treating a compound of Formula $II_b$ with (1) an acid in the presence of an inert solvent (2) followed by addition of a base (3) followed by neutralization with an acid and (4) dissolution and/or heating in an inert solvent with concomitant removal of water to give a compound of Formula I;

(i) and if desired converting the resulting compound of Formula I to a dihydroxy acid corresponding to the opened lactone ring of structural Formula I by conventional hydrolysis and further, if desired converting the dihydroxy acid to a corresponding pharmaceutically acceptable salt by conventional means, and if so desired converting the corresponding pharmaceutically acceptable salt to a dihydroxy acid by conventional means, and if so desired converting the dihydroxy acid to a compound of Formula I by heating in an inert solvent.

A second aspect of the present invention is an improved process for the preparation of the compound of Formula $I_a$

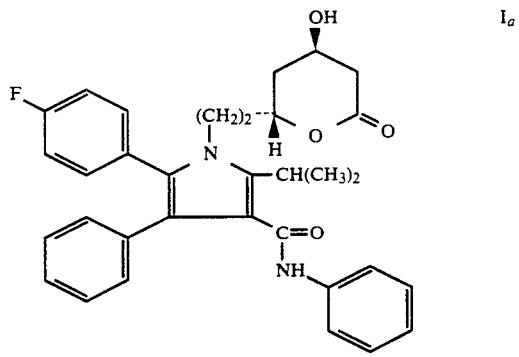

and the hydroxy acid and pharmaceutically acceptable salts thereof, corresponding to the opened lactone ring of the compound of Formula $I_a$ which comprises:

(a) reacting the compound of Formula XVII

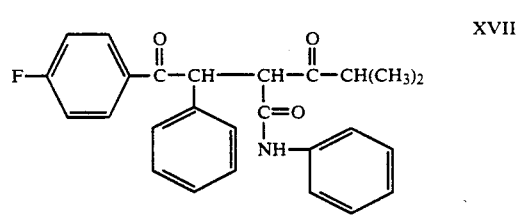

with a compound of Formula

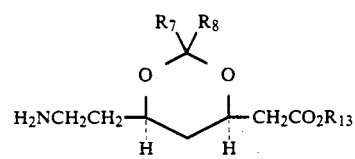

wherein $R_7$ and $R_8$ are independently hydrogen, alkyl of from one to three carbon atoms, phenyl or $R_7$ and $R_8$ are taken together as $—(CH_2)_n—$ wherein n is 4 or 5 and $R_{13}$ is hydrogen or

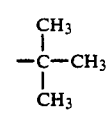

in an inert solvent and treating the resulting intermediate with an acid to afford the compound of Formula $I_a$ (b) and if desired, converting the resulting compound of Formula $I_a$ to a hydroxy acid corresponding to the opened lactone ring of structural Formula $I_a$ by conventional hydrolysis and further, if desired, converting the hydroxy acid to a corresponding pharmaceutically acceptable salt by conventional means, and if so desired, converting the hydroxy acid to a compound to Formula $I_a$ by dissolution and/or heating in an inert solvent with concomitant removal of water.

A third aspect of the present invention is an improved process for the preparation of the compound of Formula $I_a$

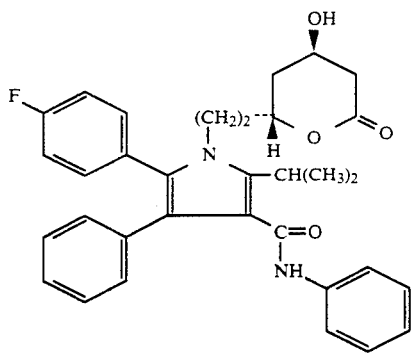

and the hydroxy acid and pharmaceutically acceptable salts thereof, corresponding to the opened lactone ring of the compound of Formula $I_a$ which comprises (a) reacting 4-methyl-3-oxo-N-phenylpentanamide with benzaldehyde in the presence of a catalyst and an inert solvent to afford the compounds of Formula XVIII

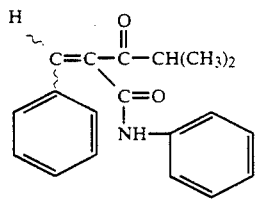

(b) reacting the compounds of Formula XVIII with 4-fluorobenzaldehyde in the presence of a catalyst, a base, and an inert solvent to afford the compound of Formula XVII

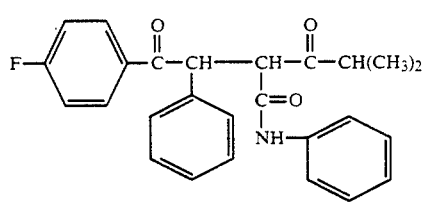

(c) reacting the compound of Formula XVII with a compound of Formula

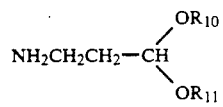

wherein $R_{10}$ and $R_{11}$ are alkyl of one to eight carbon atoms or $R_{10}$ and $R_{11}$ together are

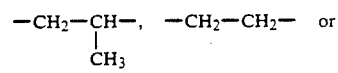

$-CH_2-CH_2-CH_2-$ in the presence of a catalyst and an inert solvent to afford a compound of Formula XVI

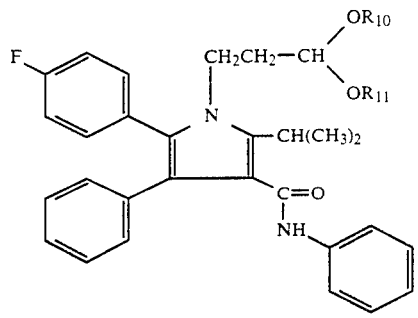

wherein $R_{10}$ and $R_{11}$ are alkyl of one to eight carbon atoms or $R_{10}$ and $R_{11}$ together are $-CH_2-CH-$, $-CH_2CH_2-$ or $-CH_2-CH_2-CH_2-$,
  |
  $CH_3$ (d) and finally converting a compound of Formula XVI in a conventional manner to afford a compound of Formula $I_a$, (e) and if desired, converting the resulting compound of Formula $I_a$ to a hydroxy acid corresponding to the opened lactone ring of structural Formula $I_a$ by conventional hydrolysis and further, if desired, converting the hydroxy acid to a corresponding pharmaceutically acceptable salt by conventional means, and if so desired, converting the hydroxy acid to a compound of Formula $I_a$ by dissolution and/or heating in an inert solvent with concomitant removal of water.

A fourth aspect of the present invention is a novel intermediate of Formula II

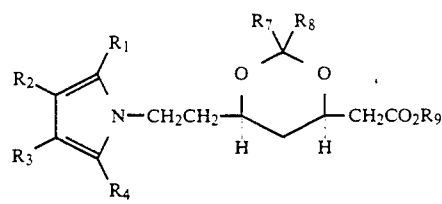

wherein $R_9$ is alkyl of from one to eight carbon atoms, a three to six-membered cycloalkyl group or α,α-dimethylbenzyl and $R_1$, $R_2$, $R_3$, $R_4$, $R_7$, and $R_8$ are as defined above, which is useful in the preparation of inhibitors of cholesterol biosynthesis of Formula I.

A fifth aspect of the present invention is a novel intermediate of Formula XVI

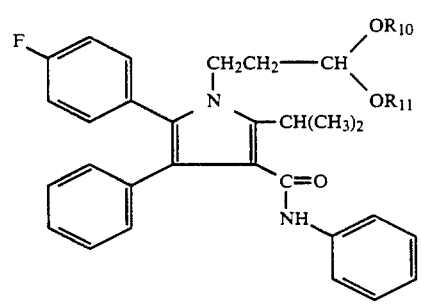

wherein $R_{10}$ and $R_{11}$ are alkyl of one to eight carbon atoms or $R_{10}$ and $R_{11}$ together are

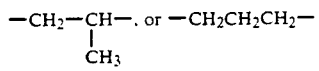

which is useful in the preparation of the inhibitor of cholesterol biosynthesis of Formula $I_a$.

A sixth aspect of the present invention is a novel intermediate of Formula IV

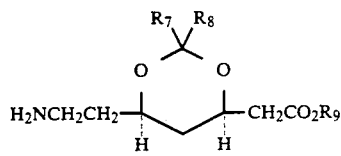

wherein $R_7$, $R_8$, and $R_9$ are as defined above, which is useful in the preparation of a compound of Formula II, which in turn is useful in the preparation of inhibitors of cholesterol biosynthesis of Formula I.

A seventh aspect of the present invention is a novel intermediate of Formula XXI

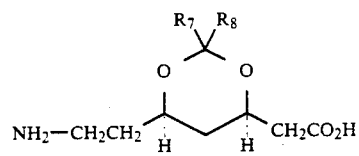

wherein $R_7$ and $R_8$ are independently hydrogen, alkyl of from one to three carbon atoms, phenyl or $R_7$ and $R_8$ are taken together as $-(CH_2)_n-$, wherein n is 4 or 5, which is useful in the preparation of the inhibitor of cholesterol biosynthesis of Formula $I_a$.

An eighth aspect of the present invention is a novel intermediate of Formula V

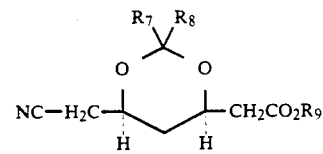

wherein $R_7$, $R_8$, and $R_9$ are as defined above, which is useful in the preparation of a compound of Formula IV, which in turn is useful in the preparation of a compound of Formula II, which in turn is useful in the preparation of inhibitors of cholesterol biosynthesis of Formula I.

A ninth aspect of the present invention is a novel intermediate of Formula VI

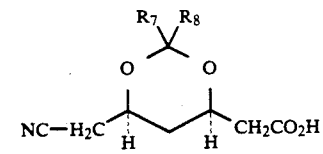

wherein $R_7$ and $R_8$ are as defined above, which is useful in the preparation of a compound of Formula V, which in turn is useful in the preparation of a compound of Formula IV, which in turn is useful in the preparation of a compound of Formula II, which in turn is useful in the preparation of inhibitors of cholesterol biosynthesis of Formula I.

A tenth aspect of the present invention is a novel intermediate of Formula VII

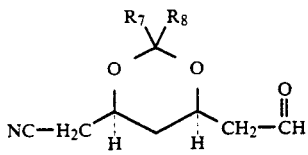

wherein $R_7$ and $R_8$ are as defined above, which is useful in the preparation of a compound of Formula VI, which in turn is useful in the preparation of a compound of Formula V, which in turn is useful in the preparation of a compound of Formula IV, which in turn is useful in the preparation of a compound of Formula II, which in turn is useful in the preparation of inhibitors of cholesterol biosynthesis of Formula I.

An eleventh aspect of the present invention is a novel intermediate of Formula VIII

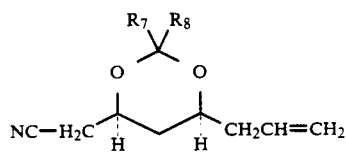

wherein $R_7$ and $R_8$ are as defined above, which is useful in the preparation of a compound of Formula VII, which in turn is useful in the preparation of a compound of Formula VI, which in turn is useful in the preparation of a compound of Formula V, which in turn is useful in the preparation of a compound of Formula IV, which in turn is useful in the preparation of a compound of Formula II which in turn is useful in the preparation of inhibitors of cholesterol biosynthesis of Formula I.

A twelfth aspect of the present invention is the novel intermediate of Formula XVII

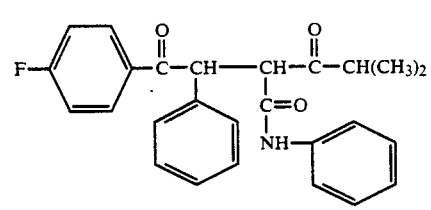

which is useful in the preparation of a compound of Formula XVI, which in turn is useful in the preparation of the inhibitor of cholesterol biosynthesis of Formula $I_a$.

A thirteenth aspect of the present invention is the novel intermediate of Formula XVIII

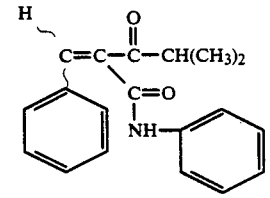

which are useful in the preparation of the compound of Formula XVII, which, in turn, is useful in the preparation of a compound of Formula XVI, which, in turn, is useful in the preparation of the inhibitor of cholesterol biosynthesis of Formula $I_a$.

DETAILED DESCRIPTION OF THE INVENTION

In this invention, the term "alkyl" means a straight or branched hydrocarbon group having from one to eight carbon atoms and includes, for example, methyl, ethyl, n-propyl, isopropyl, n-butyl, isobutyl, tertiary-butyl, n-pentyl, tertiary-amyl, n-hexyl, n-heptyl, n-octyl, and the like.

"Cycloalkyl" refers to a three- to six-membered saturated hydrocarbon ring and includes, for example, cyclobutyl, cyclopentyl, cyclohexyl, and the like.

"Alkoxy" is O-alkyl in which alkyl is as defined above.

"Alkanoyloxy" is an alkyl group, as defined above, attached to a carbonyl group and thence, through an oxygen atom, to the parent molecular residue.

"Carboalkoxy" is an alkyl group, as defined above, attached to an oxygen atom and thence, through a carbonyl group, to the parent molecular residue.

"Norbornenyl" is a group derived by the removal of a hydrogen atom (other than at a bridgehead carbon atom) from bicyclo[2.2.1]hept-2-ene.

"Halogen" is iodine, bromine, and chlorine.

"Alkali metal" is a metal in Group IA of the periodic table and includes, for example, lithium, sodium potassium, and the like.

"Alkaline-earth metal" is a metal in Group IIA of the periodic table and includes, for example, calcium, barium, strontium, and the like.

"Noble metal" is platinum, palladium, rhodium, ruthenium, and the like.

A preferred compound of Formula I prepared by the improved process of the present invention is one wherein $R_1$ is 1-naphthyl, norbornenyl, phenyl, or phenyl substituted with
fluorine,
chlorine,
bromine,
hydroxyl,
trifluoromethyl,
alkyl of from one to four carbon atoms,
alkoxy of from one to four carbon atoms, or
alkanoyloxy of from two to eight carbon atoms.

Also preferred is a compound of Formula I prepared by the improved process of the present invention wherein $R_4$ is alkyl of from one to six carbon atoms, cyclopropyl, or trifluoromethyl.

Particularly preferred compounds of Formula I prepared by the improved process of the present invention are the following:

trans-6-[2-[2-(4-fluorophenyl)-5-(trifluoromethyl)-1H-pyrrol-1-yl]ethyl]tetrahydro-4-hydroxy-2H-pyran-2-one;

trans-6[2-[2-(4-fluorophenyl)-5-methyl-1H-pyrrol-1-yl]ethyl]tetrahydro-4-hydroxy-2H-pyran-2-one;

trans-6-[2-[2-(4-fluorophenyl)-5-(1-methylethyl)-1H-pyrrol-1-yl]ethyl]tetrahydro-4-hydroxy-2H-pyran-2-one;

trans-6-[2-[2-cyclopropyl-5-(4-fluorophenyl)-1H-pyrrol-1-yl]ethyl]tetrahydro-4-hydroxy-2H-pyran-2-one;

trans-6-[2-[2-(1,1-dimethylethyl)-5-(4-fluorophenyl)-1H-pyrrol-1-yl]ethyl]tetrahydro-4-hydroxy-2H-pyran-2-one;

trans-tetrahydro-4-hydroxy-6-[2-[2-(2-methoxyphenyl)-5-methyl-1H-pyrrol-1-yl]ethyl]-2H-2-one;

trans-tetrahydro-4-hydroxy-6-[2-[2-(2-methoxyphenyl)-5-(1-methylethyl)-1H-pyrrol-1-yl]ethyl]-2H-pyran-2-one;

trans-tetrahydro-4-hydroxy-6-[2-[2-methyl-5-(1-naphthalenyl)-1H-pyrrol-1-yl]ethyl]]-2H-pyran-2-one;

trans-6-[2-(2-bicyclo[2.2.1]hept-5-en-2-yl-5-methyl-1H-pyrrol-1-yl)ethyl]tetrahydro-4-hydroxy-2H-pyran-2-one;

trans($\pm$)-5-(4-fluorophenyl)-2-(1-methylethyl)-N,4-diphenyl-1-[2-(tetrahydro-4-hydroxy-6-oxo-2H-pyran-2-yl)ethyl]-1H-pyrrole-3-carboxyamide;

(2R)-trans)-5-(4-fluorophenyl)-2-(1-methylethyl)-N,4-diphenyl-1-[2-(tetrahydro-4-hydroxy-6-oxo-2H-pyran-2-yl)ethyl]-1H-pyrrole-3-carboxamide;

trans-2-(4-fluorophenyl)-N,4-diphenyl-1-[2-tetrahydro-4-hydroxy-6-oxo-2H-pyran-2-yl)ethyl]-5-trifluoromethyl-1H-pyrrole-3-carboxamide;

trans-5-(4-fluorophenyl)-N,4-diphenyl-1-[2-(tetrahydro-4-hydroxy-6-oxo-2H-pyran-2-yl)ethyl]-2-trifluoromethyl-1H-pyrrole-3-carboxamide; and a dihydroxy acid and pharmaceutically acceptable salts thereof, corresponding to the opened lactone ring of compounds of structural Formula I.

As previously described, the compounds of Formula I are useful as inhibitors of the enzyme 3-hydroxy-3-methylglutaryl-coenzyme A reductase (HMG CoA reductase) and are thus useful as hypolipidemic or hypocholesterolemic agents.

The process of the present invention in its first aspect is a new, improved, economical, and commercially feasible method for preparing HMG CoA reductase inhibitors of Formula I. The process of the present invention in its first aspect is outlined in Scheme I:

SCHEME I

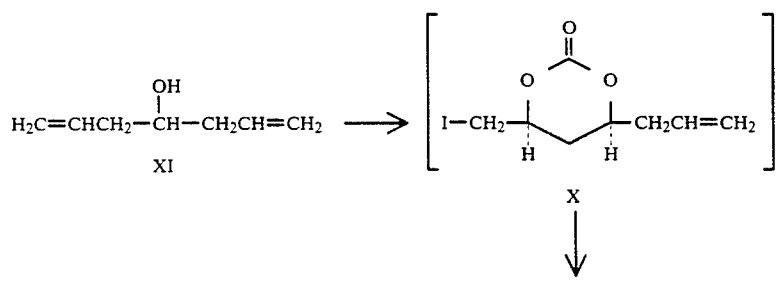

SCHEME I -continued

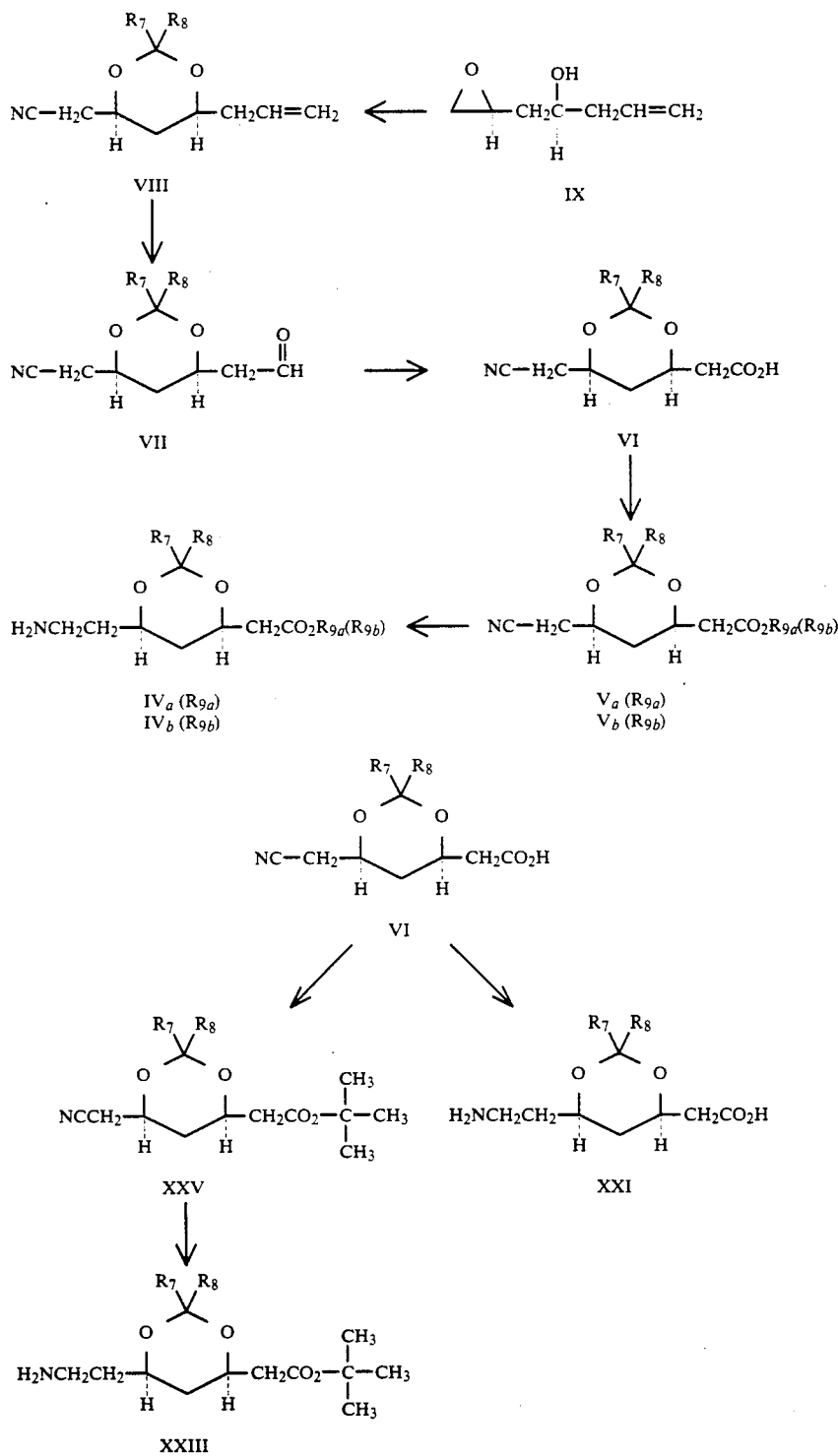

A compound of Formula IX is prepared from the known 1,6-heptadien-4-ol (XI) using the methodology described by Bongini, A., et al, *Journal of Organic Chemistry*, 47, pp 4626–4633 (1982) and Majewski, M., et al, *Tetrahedron Letters*, 25, pp 2101–2104 (1984). Thus, the homoallylic alcohol (XI) is reacted with an alkyl lithium such as, for example, n-butyllithium followed by iodine and carbon dioxide to give the iodocarbonate (X) at $-35°$ C. to $-20°$ C. which is not isolated but treated in situ with a base such as an alkali or alkaline-earth metal hydroxide or carbonate, for example, sodium hydroxide, potassium hydroxide, calcium hydroxide, sodium carbonate, potassium carbonate, calcium carbonate, and the like, in an aqueous alcohol of from one to three carbon atoms such as, for example, methanol, ethanol, isopropanol, and the like, at about 0° C. to about 40° C., to afford the epoxide of Formula IX. Preferably the reaction is carried out with potassium carbonate in aqueous methanol at about 0° C. to about 40° C., preferably 0° C. The epoxide ring of Formula IX is opened with either potassium or sodium cyanide in an aqueous alcohol such as, for example, methanol, ethanol, tertiary butanol, isopropanol, and the like, at about 0° C. to about 40° C. Preferably the reaction is carried out with potassium cyanide in aqueous isopropanol at about 25° C. The resulting diol intermediate is not isolated but treated in situ with a ketal forming reagent such as, for example, acetone, dimethoxypropane, 2-methoxypropene, benzaldehyde, cyclopentane, cyclohexanone, 1,1-dimethoxycyclopentane, 1,1-dimethoxycyclohexane, and the like, in the presence of an acid such as, for example, camphorsulfonic acid, para-toluenesulfonic acid, and the like, in the presence of excess reagent or in an inert solvent such as, for example, dichloromethane, and the like, at about 0° C. to the reflux temperature of the reagent or solvent to afford a compound of Formula VIII, wherein $R_7$ and $R_8$ are independently hydrogen, alkyl of from one to three carbon atoms, phenyl or $R_7$ and $R_8$ are taken together as $-(CH_2)_n-$, wherein n is 4 or 5. A compound of Formula VIII is treated with ozone in an inert solvent such as, for example, dichloromethane and the like, and the resulting intermediate ozonide which is not isolated is flushed in situ with oxygen to remove the ozone and then treated with triphenylphosphine or dimethyl sulfide at about $-20°$ C. to about $-78°$ C., preferably about $-78°$ C., to afford a compound of Formula VII, wherein $R_7$ and $R_8$ are as defined above. A compound of Formula VII is treated with an oxidizing reagent such as, for example, chromium trioxide-sulfuric acid-water, and the like, at about 0° C. to afford a compound of Formula VI, wherein $R_7$ and $R_8$ are as defined above. A compound of Formula VI is treated with a compound of Formula Hal—$R_{9a}$ wherein Hal is halogen such as, for example, iodine, chlorine, bromine, and $R_{9a}$ is alkyl of from one to eight carbon atoms, or a three- to six-membered cycloalkyl group, preferably isopropyl, isobutyl, and the like in the presence of a base such as, for example, 1,8-diazabicyclo[5.4.0]undec-7-ene (DBU), and the like to afford a compound of Formula $V_a$, wherein $R_7$, $R_8$, and $R_{9a}$ are as defined above. Additionally, treating the compound of Formula VI with a compound of Formula HO—$R_{9b}$ wherein $R_{9b}$ is tertiary butyl, tertiary amyl, or α,α-dimethylbenzyl in the presence of an activating agent such as, for example, dicyclohexylcarbodiimide, 1,1'-carbonyldiimidazole and the like in the presence of a base such as, for example, 4-dimethylaminopyridine and the like in an inert solvent such as, for example, dichloromethane, tetrahydrofuran, and the like to afford a compound of Formula $V_b$, wherein $R_7$, $R_8$, and $R_{9b}$ are as defined above. A compound of Formula $V_a$ is treated with hydrogen in the presence of a catalyst such as a noble metal, for example, platinum, palladium, rhodium, ruthenium, derivatives thereof, and the like, or Raney nickel, preferably platinum dioxide, and an acid, such as, for example, acetic acid, propanoic acid and the like, preferably acetic acid, at about 0° C. to about 70° C. and about 14 to about 100 pounds per square inch pressure to afford a compound of Formula $IV_a$, wherein $R_7$, $R_8$, and $R_{9a}$ are as defined above. Additionally, a compound of Formula $V_b$ is treated with hydrogen in the presence of a catalyst such as a noble metal, for example, platinum, palladium, rhodium, ruthenium, derivatives thereof, and the like, and an acid such as, for example, acetic acid, propanoic acid and the like, or a catalyst such as, for example, Raney nickel, Raney cobalt and the like, in an inert solvent such as, for example, methanol, ethanol, isopropanol, tetrahydrofuran and the like, saturated with anhydrous ammonia or saturated with aqueous ammonium hydroxide or aqueous sodium hydroxide, preferably the reaction is carried out with Raney nickel in methanol saturated with anhydrous ammonia at about 0° C. to about 70° C. and about 14 to about 100 pounds per square inch pressure to afford a compound of Formula $IV_b$, wherein $R_7$, $R_8$, and $R_{9b}$ are as defined above. Raney nickel and Raney cobalt as described above are finely divided forms of nickel and cobalt.

A compound of Formula XXI is prepared by treating a compound of Formula VI

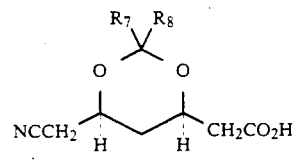

VI wherein $R_7$ and $R_8$ are as defined above with hydrogen in the presence of a catalyst such as, for example, Raney nickel, Raney cobalt and the like in finely divided form, in an inert solvent such as, for example, methanol, ethanol, isopropanol, tetrahydrofuran and the like, saturated with anhydrous ammonia or saturated with aqueous ammonium hydroxide solution or a catalyst such as, for example, platinum, palladium and the like, in an inert solvent such as, for example, methanol, ethanol, isopropanol, tetrahydrofuran and the like in the presence of an acid such as, for example, acetic acid, propanoic acid and the like, at about 0° C. to about 70° C. and about 14 to about 100 pounds per square inch pressure to afford a compound of Formula XXI.

A compound of Formula XXIII is prepared from a compound of Formula XXV

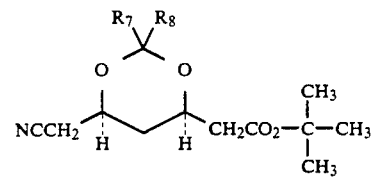

XXV wherein $R_7$ and $R_8$ are as defined above using the methodology previously described for preparing a compound of Formula XXI from a compound of Formula VI. A compound of Formula XXV is prepared by treating a compound of Formula VI

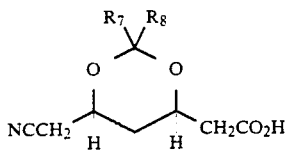

VI wherein $R_7$ and $R_8$ are as defined above and tertiary butyl alcohol with a coupling reagent such as, for example, dicyclohexylcarbodiimide and the like in the presence of a base such as, for example, 4-dimethylaminopyridine and the like in an inert solvent such as, for example dichloromethane and the like to afford a compound of Formula XXV.

An optically active (R) compound of Formula $XXIII_a$ is prepared as outlined in Scheme II. The starting material (R)-4-cyano-3-[[(1,1-dimethylethyl)dimethylsilyl]oxy]butanoic acid of Formula XXIX is synthesized starting from isoascorbic acid using syntheses well known to practitioners of the art. This chemistry is identical to that disclosed in U.S. Pat. No. 4,611,067 (Merck & Co. Inc.) using ascorbic acid which is herein incorporated by reference which produces (S)-4-cyano-3-[[(1,1-dimethylethyl)dimethylsilyl]oxy]butanoic acid.[1]

[1] U.S. Pat. No. 4,611,067 apparently incorrectly assigned the configuration R to the product of this sequence of reactions starting with ascorbic acid.

SCHEME II

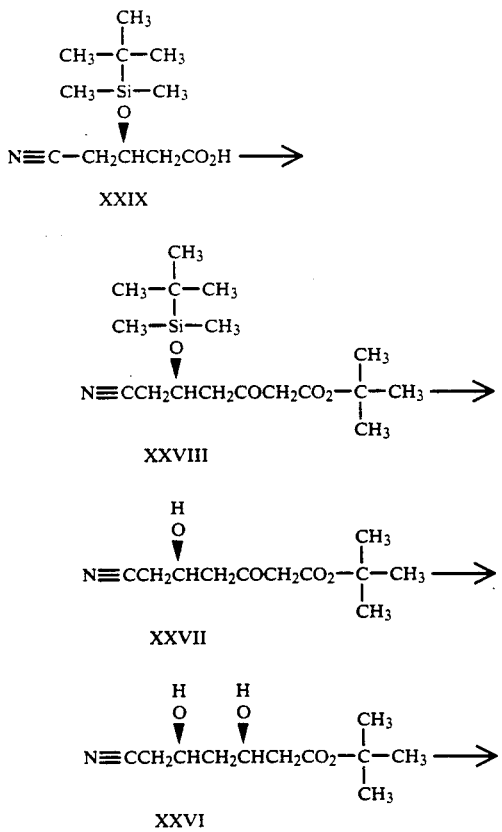

-continued
SCHEME II

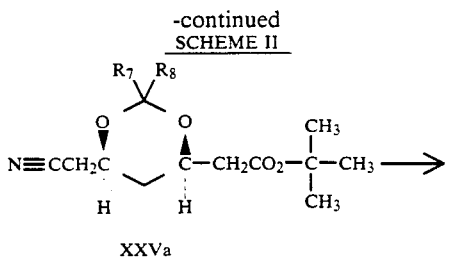

XXVa

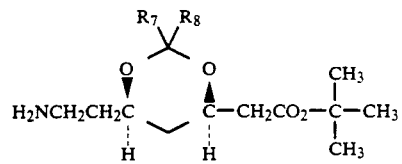

XXIIIa

Thus, the optically active compounds are prepared from the known isoascorbic acid using the methodology described by Volante R. P. et al, in U.S. Pat. No. 4,611,067 but in that case starting with ascorbic acid. This establishes the optically active centers desired in Formula $XXV_a$ and Formula $XXIII_a$ as R. Thus, the (R)-4-cyano-3-[[(1,1-dimethylethyl)dimethylsilyl]oxy]butanoic acid of Formula XXIX is treated with carbonyldiimidazole in tetrahydrofuran at 0° C. to −40° C., preferably −20° C., warmed to 25° C. and the activated acid derivative is not isolated but the solution is added to a suspension of a salt of 1,1-dimethylethyl malonic acid such as, for example, the potassium salt of 1,1-dimethylethyl malonic acid (half ester, half salt) anhydrous magnesium chloride, and an amine such as, for example, diisopropylethylamine in acetonitrile at −10° C. to 20° C. preferably at 5° C. The mixture is poured into a mixture of 1N hydrochloric acid and ethyl acetate to afford the (R)-1,1-dimethylethyl 6-cyano-5-[(1,1-dimethylethyl)dimethylsilyl]oxy-3-oxohexanoate of Formula XXVIII. The ketone of Formula XXVIII is treated with fluoride ion at 0° C. to 65° C. preferably 25° C. to afford the (R)-1,1-dimethylethyl 6-cyano-5-hydroxy-3-oxo-hexanoate of Formula XXVII. The ketone of Formula XXVII is treated with triethylborane and air (or methoxydiethylborane without air) followed by sodium borohydride and methanol in tetrahydrofuran at −78° C. to −110° C., preferably −100° C. to afford [R-(R*,R*)]-1,1-dimethylethyl 6-cyano-3,5-hydroxyhexanoate of Formula XXVI. The diol of Formula XXVI is treated with a ketal forming reagent such as, for example, acetone, dimethoxypropane, 2-methoxypropene, benzaldehyde, cyclopentanone, cyclohexanone, 1,1-dimethoxycyclopentane, 1,1-dimethoxycyclohexane and the like, in the presence of an acid such as, for example, camphorsulfonic acid, para-toluenesulfonic acid, and the like, in the presence of excess reagent or in an inert solvent such as, for example, dichloromethane, and the like, at 0° C. to the reflux temperature of the reagent or solvent to afford a compound of Formula XXVa wherein $R_7$ and $R_8$ are independently hydrogen, alkyl of from one to three carbon atoms, phenyl or $R_7$ and $R_8$ are taken together, as $-(CH_2)_n-$, wherein n is 4 or 5.

A compound of Formula XXVa is treated with hydrogen gas in an alcohol such as methanol saturated with anhydrous ammonia or aqueous ammonium hydroxide in the presence of a catalyst such as Raney nickel or Raney cobalt or with a nobel metal catalyst such as platinum oxide in the present of an alkanoic acid such as acetic acid to afford a compound of Formula XXIII$_a$, wherein R$_7$ and R$_8$ as defined above.

Additionally, an optically active compound of Formula IV$_a$ or Formula IV$_b$ may be prepared starting from the optically active epoxide of Formula IX. The preparation of the optically active epoxide of Formula IX is described by Kocienski, P. J., et al, *Journal of the Chemical Society Perkin Transaction I*, pp 2183–2187 (1987).

The process of preparing a compound of Formula I is outlined in Scheme III:

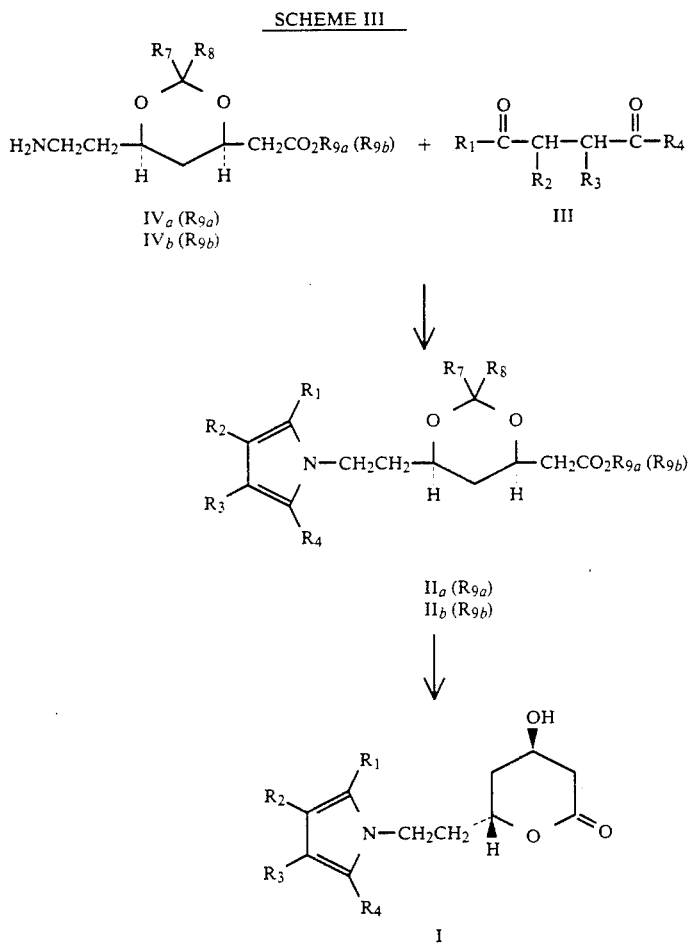

A compound of Formula IV$_a$ or Formula IV$_b$ is reacted with a compound of Formula III, wherein R$_1$ is
1-naphthyl,
2-naphthyl,
cyclohexyl,
cyclohexylmethyl,
norbornenyl,
phenyl,
phenyl substituted with
    fluorine,
    chlorine,
    bromine,
    hydroxyl,
    trifluoromethyl,
    alkyl of from one to four carbon atoms,
    alkoxy of from one to four carbon atoms, or
    alkanoyloxy of from two to eight carbon atoms,
benzyl,
2-, 3-, or 4-pyridinyl, or
2-, 3-, or 4-pyridinyl-N-oxide;
R$_2$ or R$_3$ is independently
hydrogen
alkyl of from one to six carbon atoms,
cyclopropyl,
cyclobutyl,
cyclopentyl,
cyclohexyl,
phenyl,
phenyl substituted with
    fluorine,
    chlorine,
    bromine,
    hydroxyl,
    trifluoromethyl,
    alkyl of from one to four carbon atoms, or
    alkoxy of from one to four carbon atoms,
cyano,
trifluoromethyl, or —CONR$_5$R$_6$ where R$_5$ and R$_6$ are
    independently
    hydrogen,
    alkyl of from one to six carbon atoms,
    phenyl,
    phenyl substituted with
        fluorine,
        chlorine,
        bromine,
        cyano, or
        trifluoromethyl;

R4 is
alkyl of from one to six carbon atoms,
cyclopropyl,
cyclobutyl,
cyclopentyl,
cyclohexyl, or
trifluoromethyl;
in an inert solvent such as, for example, toluene, and the like, at the reflux temperature of the solvent to give a compound of Formula II$_a$, or Formula II$_b$, wherein R$_1$, R$_2$, R$_3$, R$_4$, R$_7$, R$_8$, R$_{9a}$ and R$_{9b}$ are as defined above. Finally, a compound of Formula II$_a$ is treated with an acid such as, for example, aqueous hydrochloric acid, and the like, in an inert solvent such as, for example, tetrahydrofuran, followed by hydrolysis with a base such as, for example sodium hydroxide. The reaction is neutralized with an acid such as, for example, aqueous hydrochloric acid and dissolved and/or heated in an inert solvent such as, for example, toluene, and the like, with concomitant removal of water to give a compound of Formula I, wherein R$_1$, R$_2$, R$_3$, and R$_4$ are as defined above.

Additionally, a compound of Formula II$_b$ is treated with an acid such as, for example, aqueous hydrochloric acid, and the like, in an inert solvent such as, for example, tetrahydrofuran and the like for about 15 hours, followed by the addition of a base such as, for example, sodium hydroxide and the like and stirred for about 30 hours. The reaction is reacidified with an acid such as, for example, aqueous hydrochloric acid and dissolved and/or heated in an inert solvent such as, for example, toluene and the like, with concomitant removal of water to give a compound of Formula I, wherein R$_1$, R$_2$, R$_3$, and R$_4$ are as defined above.

The process of the present invention in its second aspect is a new, improved, economical, and commercially feasible method for preparing the HMG CoA reductase inhibitor of Formula I$_a$. The process of the present invention in its second aspect is outlined in Scheme IV:

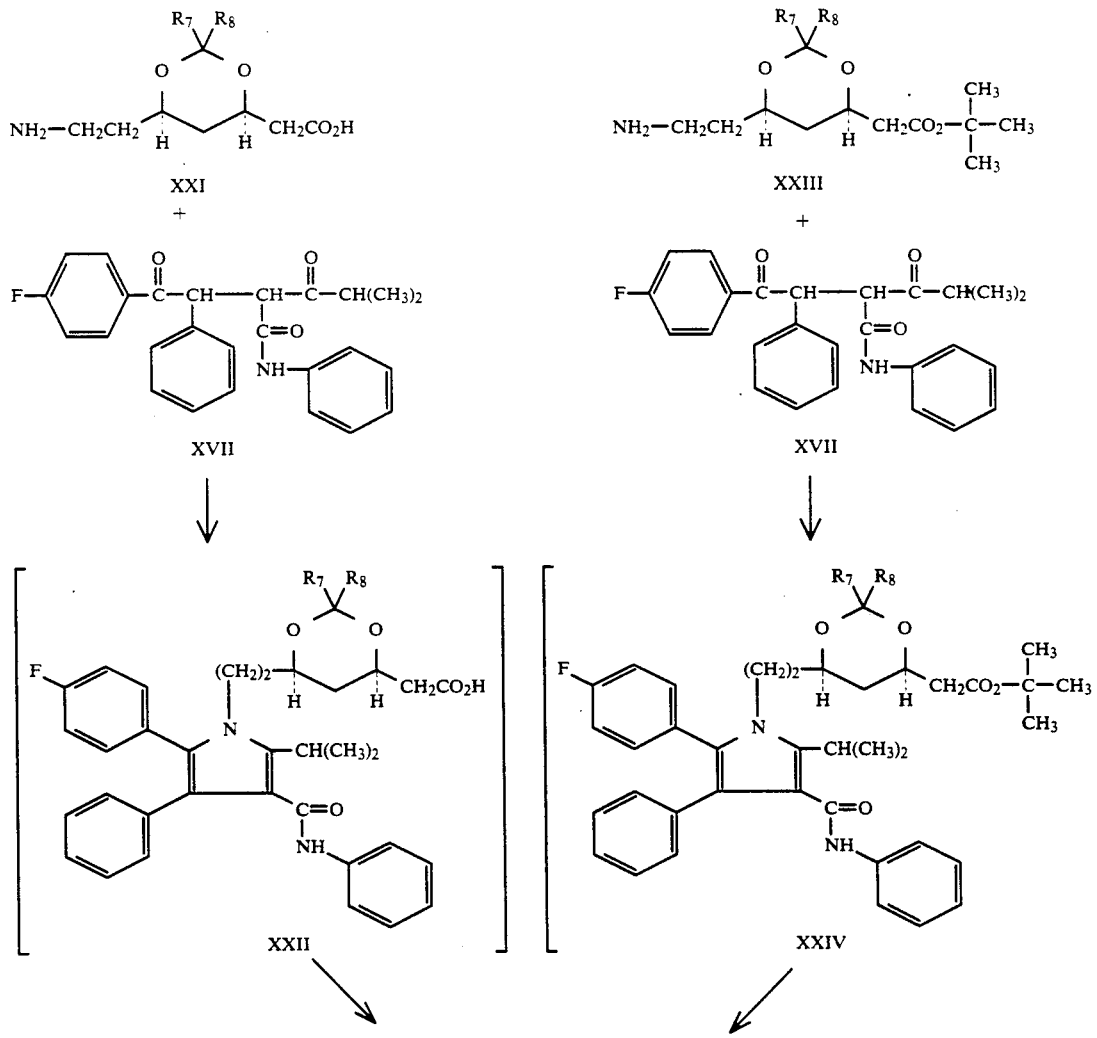

SCHEME IV

-continued
SCHEME IV

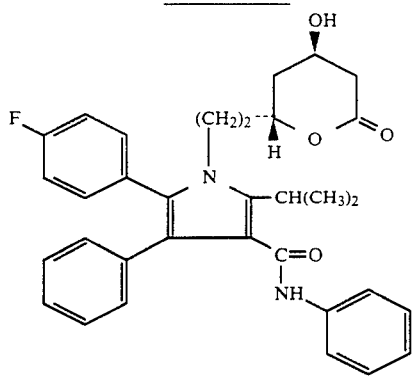

Ia

The compound of Formula XVII is reacted with a compound of Formula XXI

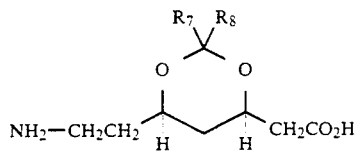

XXI wherein $R_7$ and $R_8$ are independently hydrogen, alkyl of from one to three carbon atoms, phenyl or $R_7$ and $R_8$ are taken together as —$(CH_2)_n$— wherein n is 4 or 5 in the presence of an inert solvent such as, for example, dimethyl sulfoxide and the like for about 15 hours at about 105° C. with the removal of water to afford the intermediate derivative (XXII). Preferably the reaction is carried out in dimethyl sulfoxide for about 15 hours at about 105° C. The intermediate derivative XXII, which is not isolated, is treated with an acid such as, for example, concentrated hydrochloric acid and the like in an inert solvent such as, for example, ethyl acetate and the like to afford the compound of Formula $I_a$. Preferably, the reaction is carried out with concentrated hydrochloric acid in ethyl acetate.

Additionally, the compound of Formula XVII is reacted with a compound of Formula XXIII

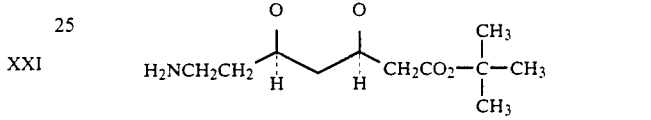

XXIII wherein $R_7$ and $R_8$ are independently hydrogen, alkyl or from one to three carbon atoms, phenyl or $R_7$ and $R_8$ are taken together as —$(CH_2)_n$—, wherein n is 4 or 5 in the presence of an inert solvent or solvents such as, for example, hexane, toluene and the like for about 24 hours at about the reflux temperature of the solvent or solvents. The intermediate derivative XXIV, which is not isolated, is treated with an acid such as, for example, a 10% aqueous solution of hydrochloric acid for about 15 hours, followed by the addition of a base such as, for example, sodium hydroxide and the like and reacidification with an acid for about 30 hours to afford the compound of Formula $I_a$.

The process of the present invention in its third aspect is a new, improved, economical, and commercially feasible method for preparing the HMG CoA reductase inhibitor of Formula $I_a$. The process of the present invention in its third aspect is outlined in Scheme V:

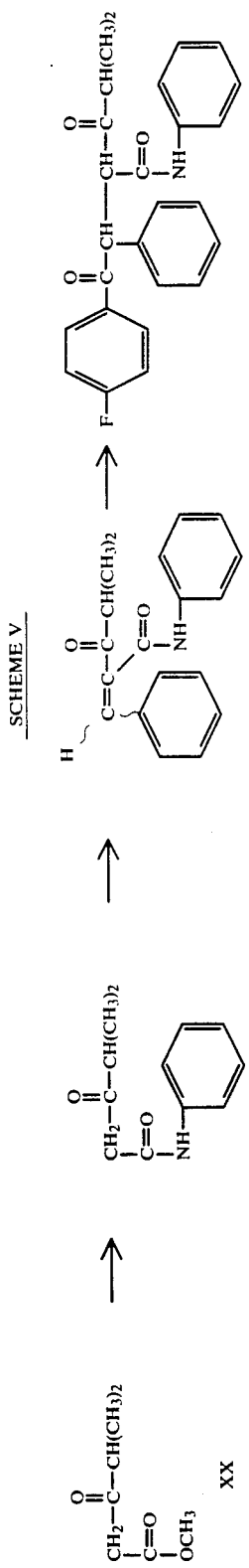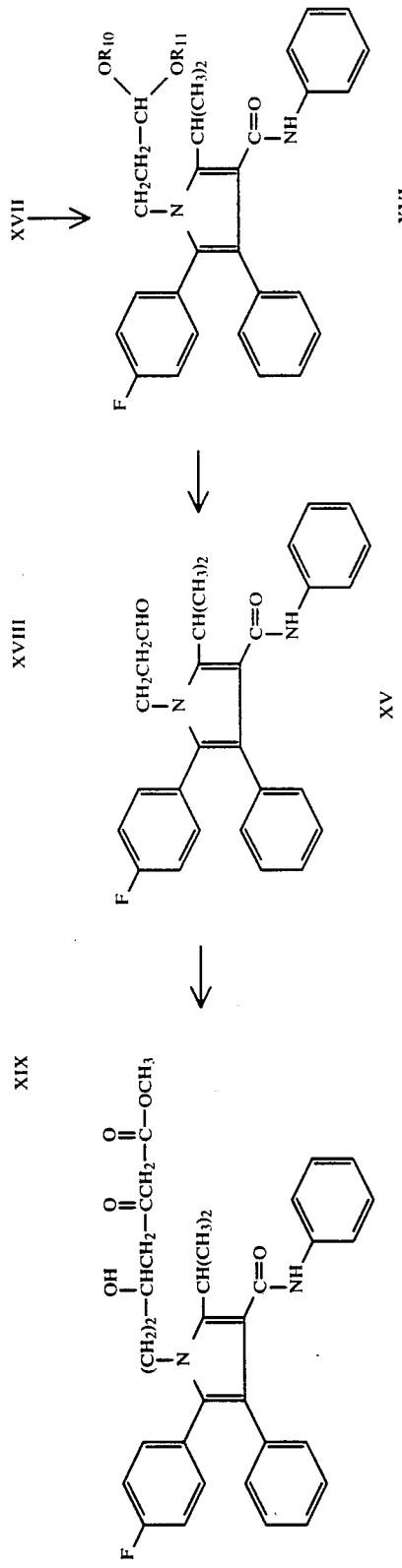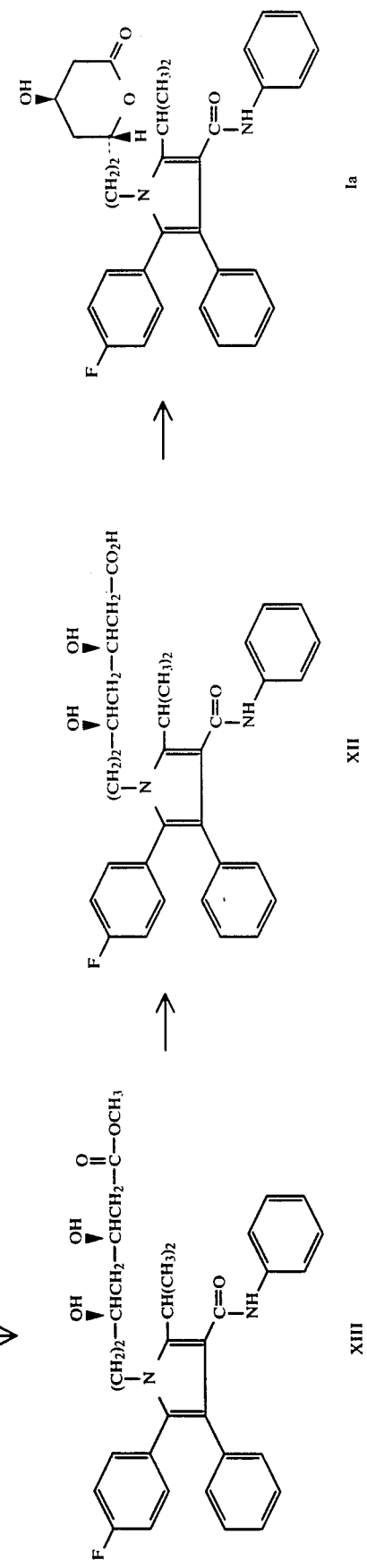

4-Methyl-3-oxo-N-phenylpentanamide (XIX) is obtained by heating a mixture of methyl 4-methyl-3-oxopentanoate (XX), aniline and ethylene diamine in toluene. 4-Methyl-3-oxo-N-phenylpentanamide (XIX) is subsequently reacted with benzaldehyde in the presence of a catalyst such as, for example, piperidine and glacial acetic acid, ethylene diamine and glacial acetic acid, β-alanine and glacial acetic acid, and the like in an inert solvent such as, for example, toluene, heptane, hexane, and the like for about 24 to about 36 hours at about 60° to about 120° C. with the removal of water to afford 4-methyl-3-oxo-N-phenyl-2-(phenylmethylene)-pentanamide (XVIII). Preferably the reaction is carried out with β-alanine and glacial acetic acid at reflux for about 24 hours in hexane. The 4-methyl-3-oxo-N-phenyl-2-(phenylmethylene)pentanamide (XVIII) is reacted with 4-fluorobenzaldehyde in the presence of a catalyst such as, for example, 3-benzyl-5-(2-hydroxyethyl)-4-methylthiazolium chloride, 3,4-dimethyl-5-(2-hydroxyethyl)thiazolium iodide, 3-ethyl-5-(2-hydroxyethyl)-4-methylthiazolium bromide, thiamine hydrochloride, and the like, and a base such as, for example, N,N-diisopropylethylamine, pyridine, N,N-dimethylaniline, triethylamine, 1,8-diazabicyclo[5.4.0]undec-7-ene (DBU), 1,4-diazabicyclo[2.2.2]octane (DABCO), 4-dimethylaminopyridine (DMAP), N,N,N',N'-tetramethylethylenediamine (TMEDA) and the like, either neat or in the presence of a solvent such as, for example, tetrahydrofuran, tertiary-butyl methyl ether, ethanol, dimethylformamide, dimethylsulfoxide, N-methylpyrrolidone, acetonitrile, methylisobutyl ketone, ethyl acetate, isopropanol, pyridine and the like for about 20 to about 30 hours under anhydrous conditions at about room temperature to about the reflux temperature of the solvent to afford the compound of Formula XVII. Preferably the reaction is carried out in the presence of 3-ethyl-5-(2-hydroxyethyl)-4-methylthiazolium bromide and triethylamine in ethanol at about 75°-80° C. for about 24 hours. The compound of Formula XVII is reacted with a compound of Formula

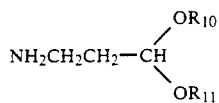

wherein $R_{10}$ and $R_{11}$ are alkyl of one to eight carbon atoms or $R_{10}$ and $R_{11}$ together are

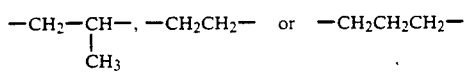

in the presence of a catalyst of Formula

wherein $R_{12}$ is $CH_3$, $CF_3$, $ClCH_2—$, $C_6H_5CH_2CH_2—$, $C_6H_5CH_2—$, $HO_2CCH_2—$, $HO_2CCH_2CH_2—$, $C_6H_5—$, para-Cl—$C_6H_5—$, $ClCH_2CH_2—$, meta-$H_3C$—$C_6H_5—$, para-$H_3C$—$C_6H_5—$, tertiary-$C_4H_9—$ or triethylamine hydrochloride and a solvent or mixtures thereof such as, for example, tetrahydrofuran, hexane, toluene, ethanol, tertiary-butyl acetate, ethyl acetate, 1,2-dichloroethane, isopropanol, dimethyl sulfoxide and the like for about 24 to about 48 hours at about 5° C. to about the reflux temperature of the solvent with the removal of water to afford a compound of Formula XVI. Preferably, the reaction is carried out in the presence of pivalic acid and a mixture of toluene and heptane at reflux for about 48 hours with the removal of water. A compound of Formula XVI is converted in a conventional manner using the methodology disclosed in U.S. Pat. No. 4,681,893 to the compound of Formula $I_a$.

Certain of the compounds of Formula III are either known or capable of being prepared by methods known in the art. The ring-opened dihydroxy acids of formula

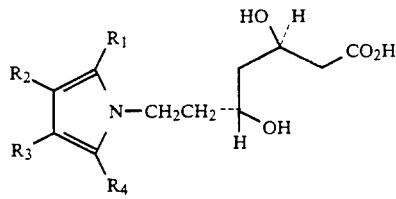

wherein $R_1$, $R_2$, $R_3$, and $R_4$ are as defined above may be prepared from the lactone compounds of Formula I by conventional hydrolysis such as, for example, sodium hydroxide in methanol, sodium hydroxide in tetrahydrofuran-water, and the like, of the lactone compounds of Formula I.

The ring-opened dihydroxy acid of Formula XII may be produced from the lactone compound of Formula $I_a$ by conventional hydrolysis of the lactone compound of Formula $I_a$.

In the ring-opened dihydroxy acid form, compounds of the present invention react to form salts with pharmaceutically acceptable metal and amine cations formed from organic and inorganic bases. The term "pharmaceutically acceptable metal salt" contemplates salts formed with the sodium, potassium, calcium, magnesium, aluminum, iron, and zinc ions. The term "pharmaceutically acceptable amine salt" contemplates salts with ammonia and organic nitrogenous bases strong enough to form salts with carboxylic acids. Bases useful for the formation of pharmaceutically acceptable nontoxic base addition salts of the compound of the present invention form a class whose limits are readily understood by those skilled in the art.

The dihydroxy free acid form of the compounds of the invention may be regenerated from the salt form, if desired, by contacting the salt with a dilute aqueous solution of an acid such as hydrochloric acid.

The ring closed lactone form of the compounds of the invention may be regenerated by dissolution of the dihydroxy acid form of the compounds of the invention in an inert solvent such as, for example, toluene, benzene, ethyl acetate, and the like, at about 0° C. to about the boiling point of the solvent usually but not necessarily with concomitant removal of the resulting water and usually but not necessarily with strong acid catalysis such as, for example, concentrated hydrochloric acid and the like.

The base addition salts may differ from the free acid forms of the compounds of this invention in such physical characteristics as solubility and melting point, but are otherwise considered equivalent to the free acid form for the purposes of this invention.

The compounds of the present invention may exist in solvated or unsolvated form and such forms are equivalent to the unsolvated form for the purposes of this invention.

The compounds of structural Formulas I, I$_a$, and XII above possesses two asymmetric carbon centers, one at the 4-hydroxy position of the pyran-2-one ring, and the other at the 6-position of the pyran-2-one ring where the alkylpyrrole group is attached. This asymmetry gives rise to four possible isomers, two of which are the 4R,6S and 4S,6R-isomers and the other two of which are the 4R,6S and 4S,6S-isomers. The preferred isomer in this invention is the 4R,6R-isomer of the compounds of Formulas I, I$_a$ and XII above.

The following nonlimiting examples illustrates the inventors' preferred method for preparing the compounds of the invention.

EXAMPLE 1

Trans-6-[2-[2-ethyl-5-(4-fluorophenyl)-1H-pyrrol-1-yl]ethyl]-tetrahydro-4-hydroxy-2H-pyran-2-one.

Step A: Preparation of (R*,R*)-α-2-propenyloxiraneethanol.

n-Butyllithium, 129 mL (200 mmol), is added dropwise to a 0° C. solution of 1,6-heptadien-4-ol, 22.4 g (0.2 mol), in 200 mL of anhydrous tetrahydrofuran until the triphenylmethane indicator turned red. Carbon dioxide is then bubbled in for 30 minutes (lecture bottle carbon dioxide passed through drierite) and the light yellow solution is stirred for 30 minutes under a balloon of carbon dioxide. To this solution is added iodine, 101.4 g (0.4 mol), dissolved in ~200 mL of anhydrous tetrahydrofuran over 60 minutes. The mixture is allowed to warm to room temperature overnight, diluted with ethyl acetate, washed with 10% sodium bisulfite solution, saturated solution of sodium bicarbonate, brine, and dried (magnesium sulfate). The crude product is dissolved in 200 mL of methanol and 20 mL of water, cooled to 0° C. and 0.5 g of solid potassium carbonate is added. The mixture is vigorously stirred for six hours, filtered, concentrated, and partitioned between ethyl acetate and brine. After extracting the aqueous layer 2× with ethyl acetate, the combined organics are washed with brine and dried (magnesium sulfate). Flash chromatography (4:1 hexane-ethyl acetate) provides, after concentration in vacuo, 18 g of (R*,R*)-α-b 2-propenyloxiraneethanol.

200 MHz NMR (CDCl$_3$) δ1.5–1.65 (m, 1H), 1.90 (dt, 1H, J=15, 4 Hz), 2.2 (m, 3H), 2.53 (m, 1H), 2.79 (m, 1H), 3.12 (m, 1H), 3.94 (m, 1H), 5.19 (m, 2H), 5.80 (m, 1H).

IR (film) 3400, 3077, 2980, 2925, 1643, 1412, 1260, 918, 827 cm$^{-1}$.

Step B: Preparation of (±)-cis-2,2-dimethyl-6-(2-propenyl)-1,3-dioxane-4-acetonitrile.

Potassium cyanide, 1.3 g (20 mmol), is added to a room temperature solution of (R*,R*)-α-2-propenyloxiraneethanol, 2.56 g (20 mmol), in 25 mL of 4:1 isopropanol-water. The solution is stirred for 20 hours at ambient temperature, concentrated, and partitioned between ethyl acetate and brine. The aqueous layer is extracted 2× with ethyl acetate and the combined ethyl acetate extracts are washed with brine and dried (magnesium sulfate). The crude product is dissolved in 20 mL of 2,2-dimethoxypropane, camphorsulfonic acid is added and the solution stirred for 18 hours at room temperature. Concentration and flash chromatography provides 1.30 g of (±)-cis-2,2-dimethyl-6-(2-propenyl)-1,3-dioxane-4-acetonitrile.

200 MHz NMR (CDCl$_3$) δ1.35 (m, 1H), 1.40 (s, 3H), 1.45 (s, 3H), 1.67 (m, 1H), 2.20 (m, 1H), 2.33 (m, 1H), 2.50 (m, 2H), 3.89 (m, 1H), 4.10 (m, 1H), 5.10 (m, 2H), 5.7–5.9 (m, 1H).

IR (film) 2995, 2944, 2255, 1644, 1334 cm$^{-1}$.

Step C: Preparation of (±)-cis-6-(2-oxoethyl)-2,2-dimethyl-1,3-dioxane-4-acetonitrile.

A solution of (±)-cis-2,2-dimethyl-6-(2-propenyl)-1,3-dioxane-4-acetonitrile, 3 g (15.36 mmol), in 100 mL of dichloromethane is cooled to −78° C. under nitrogen. Ozone (Welsbach generator, flow rate 0.1, voltage=90 V) is then passed through a fritted gas inlet tube into the solution until the blue color of ozone appears. The current is turned off, and oxygen bubbled through until the blue color is discharged. Triphenylphosphine, 4.2 g (16 mmol), is added and the colorless solution allowed to warm to room temperature. Flash chromatography provides, after concentration in vacuo, 2.5 g of pure (±)-cis-6-(2-oxoethyl)-2,2-dimethyl-1,3-dioxane-4-acetonitrile.

200 MHz NMR (CDCl$_3$) δ1.30 (m, 1H), 1.39 (s, 3H), 1.48 (s, 3H), 1.78 (m, 1H), 2.46–2.75 (m, 4H), 4.2 (m, 1H), 4.40 (m, 1H), 9.79 (t, 1H, J=1.6 Hz).

IR (film) 2250, 1720 cm$^{-1}$.

Step D: Preparation of (±)-cis-6-(cyanomethyl)-2,2-dimethyl-1,3-dioxane-4-acetic acid.

Jones reagent (chromium trioxide-sulfuric acid-water), 3.8 mL (7.6 mmol), is added dropwise to a 0° C. solution of (±)-cis-6-(2-oxoethyl)-2,2-dimethyl-1,3-dioxane-4-acetonitrile, 1.50 g (7.6 mmol), dissolved in 50 mL of acetone until the orange color is not discharged. After stirring a further 15 minutes, the mixture is poured into 300 mL of diethyl ether and washed with brine until the aqueous washes are colorless. The diethyl ether layer is dried (magnesium sulfate), filtered, and concentrated to provide 1.2 g of the acid which solidifies on standing. Trituration with isopropyl ether provides (±)-cis-6-(cyanomethyl)-2,2-dimethyl-1,3-dioxane-4-acetic acid as a colorless solid; mp 92°–95° C. A second trituration/recrystallation from isopropyl ether provides material of mp 98°–103° C.

200 MHz NMR (CDCl$_3$) δ1.35 (m, 1H), 1.42 (s, 3H), 1.49 (s, 3H), 1.82 (m, 1H), 2.4–2.7 (m, 4H), 4.18 (m, 1H), 4.35 (m, 1H).

$^{13}$C-NMR(d$_6$-acetone, 50 MHz) δ19.95, 24.91, 30.17, 35.88, 41.34, 65.79, 66.35, 99.70, 117.77, 171.83.

IR (KBr) broad OH 3500–2400, 2254, 1711, 940 cm$^{-1}$.

Step E: Preparation of (±)-cis-1-methylethyl 6-cyanomethyl)-2,2-dimethyl-1,3-dioxane-4-acetate.

To a solution of (±)-cis-6-(cyanomethyl)-2,2-dimethyl-1,3-dioxane-4-acetic acid, 0.6 g (3 mmol), in acetonitrile, 2 mL, is added 1,8-diazabicyclo[5.4.0]undec-7-ene (DBU), 0.45 mL (3 mmol), and 2-iodopropane, 0.33 mL (3.3 mmol). The solution is stirred overnight at room temperature, diluted with diethyl ether, washed with brine, and dried (magnesium sulfate). Flash chromatography provides 0.55 g of (±)-cis-1-methylethyl-6-(cyanomethyl)-2,2-dimethyl-1,3-dioxane-4-acetate.

90 MHz NMR (CDCl$_3$) δ1.22 (d, 6H, J=7 Hz), 1.3 (m, 1H), 1.35 (s, 3H), 1.40 (s, 3H), 1.75 (m, 1H), 2.2–2.7 (m, 4H), 3.9–4.4 (m, 2H), 4.95 (septet, 1H, J=7 Hz).

Step F: Preparation of (±)-cis-1-methylethyl 6-(2-aminoethyl)-2,2-dimethyl-1,3-dioxane-4-acetate.

A mixture of (±)-cis-1-methylethyl 6-(cyanomethyl)-2,2-dimethyl-1,3-dioxane-4-acetate, 0.55 g, in glacial acetic acid is hydrogenated with platinum dioxide at 50 pounds per square inch (PSI). Concentration, dilution with ethyl acetate and bicarbonate wash, followed by washing with brine and drying provides 250 mg of (±)-cis-1-methylethyl 6-(2-aminoethyl)-2,2-dimethyl-1,3-dioxane-4-acetate. MS 260.1, 244.1

200 MHz NMR (CDCl$_3$) δ1.25 (d, 6H, J=7 Hz), 1.32 (m, 1H), 1.36 (s, 3H), 1.45 (s, 3H), 1.60 (m, 1H), 2.33 (dd, 1H, J=15, 6 Hz), 2.49 (dd, 1H, J=15, 6 Hz), 2.85 (br t, 2H, J=6 Hz), 3.40 (br s, 2H), 4.00 (m, 1H), 4.29 (m, 1H), 12.03 (septet, 1H, J=7 Hz).

IR (film) 1734, 1387 cm$^{-1}$.

Step G: Preparation of (±)-cis-1-methylethyl 6-[2-[2-ethyl-5-(4-fluorophenyl)-1H-pyrrol-1-yl]ethyl]-2,2-dimethyl-1,3-dioxane-4-acetate.

A solution of (±)-cis-1-methylethyl 6-(2-aminoethyl)-2,2-dimethyl-1,3-dioxane-4-acetate, 0.15 g (0.58 mmol), and 1-(4-fluorophenyl)-1,4-hexanedione (Example A), 0.125 g (0.6 mmol), in 5 mL of toluene is stirred and heated at reflux overnight. The cooled solution is concentrated and the highly UV active pyrrole is separated from starting material by preparative thin layer chromatography, eluting 2× with 4:1 hexane-ethyl acetate. This provides 130 mg of pure (±)-cis-1-methylethyl 6-[2-[2-ethyl-5-(4-fluorophenyl)-1H-pyrrol-1-yl]ethyl]-2,2-dimethyl-1,3-dioxane-4-acetate.

200 MHz NMR (CDCl$_3$) δ1.51 (m, 1H), 1.23 (d, 6H, J =6 Hz), 1.33 (m, 9H), 1.5-1.6 (m, 1H), 2.27 (dd, 1H, J=15.3, 6 Hz), 2.44 (dd, 1H, J=15.3, 6 Hz), 2.66 (q, 2H, J=7.5 Hz), 3.62 (m, 1H), 3.8-4.2 (m, 3H), 5.03 (septet, 1H, J=6 Hz), 5.97 (d, 1H, J=3.5 Hz), 6.11 (d, 1H, J=3.5 Hz), 7.0-7.4 (m, 4H).

A solution of (±)-cis-1-methylethyl 6-[2,2-ethyl-5-(4-fluorophenyl)-1H-pyrrol-1-yl]ethyl]-2,2-dimethyl-1,3-dioxane-4-acetate, 0.13 g (0.3 mmol), in 12 mL of 1:2 2M hydrochloric acid-tetrahydrofuran is stirred overnight at room temperature. To this is added sufficient 2M sodium hydroxide to bring the pH to 10. Stirring is continued for 30 minutes, water, 30 mL, is added and the mixture is extracted with diethyl ether. The aqueous layer is acidified with ice cold 6N hydrochloric acid and extracted with ethyl acetate (2×). The organic layer is washed with brine and dried (magnesium sulfate). The residue which remains on filtration and concentration is dissolved in toluene (50 mL) and heated at reflux with azeotropic removal of water (6 hours). The cooled solution is concentrated and flash chromatographed to provide 60 mg of trans-6-[2-[2-ethyl-5-(4-fluorophenyl)-1H-pyrrol-1-yl]ethyl]-tetrahydro-4-hydroxy-2H-pyran-2-one (elution with 2:1 hexane-ethyl acetate).

90 MHz NMR (CDCl$_3$) δ1.25 (d, 6H, J=7 Hz) 1.3-1.8 (m, 4H), 2.3 (br s, 1H, —OH), 2.55 (m, 2H), 2.65 (q, 2H, J=7 Hz), 3.9-4.5 (m, 4H), 5.90 (d, 1H, J=3.5 Hz), 6.05 (d, 1H, J=3.5 Hz), 6.9-7.4 (m, 4H).

EXAMPLE 2

Trans-(±)-5-(4-fluorophenyl)-2-(1-methylethyl)-N,4-diphenyl-1-[2-(tetrahydro-4-hydroxy-6-oxo-2H-pyran-2-yl)ethyl]-1H-pyrrole-3-carboxamide.

METHOD A

Step A: Preparation of 4-Methyl-3-oxo-N-phenyl-2-(phenylmethylene)pentanamide.

A suspension of 100 kg of 4-methyl-3-oxo-N-phenylpentanamide (Example B) in 660 kg of hexanes is treated with agitation under nitrogen with 8 kg of β-alanine, 47 kg of benzaldehyde, and 13 kg of glacial acetic acid. The resulting suspension is heated to reflux with removal of water for 20 hours. An additional 396 kg of hexanes and 3 kg of glacial acetic acid is added and reflux continued with water removal for one hour. The reaction mixture is cooled to 20°-25° C. and the product is isolated by filtration. The product is purified by slurrying in hexanes at 50°-60° C., cooling, and filtration. The product is slurried twice with water at 20°-25° C., filtered, and dried in vacuo to yield 110 kg of 4-methyl-3-oxo-N-phenyl-2-(phenylmethylene)pentanamide, mp 143.7°-154.4° C.

Vapor Phase Chromatography (VPC): 30 meter DB 5 capillary column 50°-270° C. at 15° C./min. 19.33 min, 99.7% (area.

Gas Chromatography/Mass Spectrometry (GC/MC): M/Z 293 [M]$^+$.

Nuclear Magnetic Resonance (NMR): (CDCl$_3$) δ1.16 (6H, d), 3.30 (1H, quin.), 7.09 (1H, m), 7.28 (5H, m), 7.49 (5H, m), 8.01 (1H, brs).

Step B: Preparation of (±)4-Fluoro-α-[2-methyl-1-oxopropyl]-γ-oxo-N,β-diphenylbenzenebutaneamide mixture of [R-(R*,R*)], [R-(R*,S*)], [S-(R*,R*)] and [S-(R*,S*)] isomers.

A solution of 17.5 kg of 3-ethyl-5-(2-hydroxyethyl)-4-methylthiazolium bromide in 300 L of anhydrous ethanol is concentrated by distillation of 275 L of the ethanol. Under an argon atmosphere, 100 kg (340 mol) of 4-methyl-3-oxo-N-phenyl-2-(phenylmethylene)pentanamide, 47.5 L (340 mol) of triethylamine, and 40 L (375 mol) of 4-fluorobenzaldehyde are added. The resulting solution is stirred and heated at 75°-80° C. for 23 hours. The product begins to form as a solid after approximately 1.5 hours but approximately 24 is required for essentially complete conversion. The slurry is dissolved in 600 L of isopropanol at 80° C. The resulting solution is slowly cooled and the (±)4-fluoro-α-[2-methyl-1-oxopropyl]-γ-oxo-N,β-diphenylbenzenebutaneamide mixture of [R-(R*,R*)], [R-(R*,S*)], [S-(R*,R*)] and [S-(R*,S*)] isomers isolated by filtration. Washing the precipitate with isopropanol and drying in vacuo yielded 99 kg of (±)4-fluoro-α-[2-methyl-1-oxopropyl]-γ-oxo-N,β-diphenylbenzenebutaneamide mixture of [R-(R*,R*)], [R-(R*,S*)], [S-(R*,R*)] and [S-(R*,S*)] isomers; mp 206.8°-207.6° C.

NMR: (CDCl$_3$) δ1.03 (3H, d), 1.22 (3H, d), 2.98 (1H, quin.), 4.91 (1H, d, J=11 Hz), 5.51 (1H, d, J=11 Hz), 6.98-7.43 (12H, m), 8.17 (2H, dd), 9.41 (1H, brs).

High Pressure Liquid Chromatography (HPLC): (Acetonitrile:tetrahydrofuran:water)(40:25:55) Econosil C$_{18}$5 μ25 cm 1.0 mL/min. 254 nm 16.77 min. 99.2% (area).

Step C: Preparation of 1-(3,3-Diethoxypropyl)-5-(4-fluorophenyl)-2-(1-methylethyl)-N,4-diphenyl-1H-pyrrole-3-carboxamide.

To a nitrogen purged flask equipped with a mechanical stirrer is added 130 kg (311 mol) of (±)4-fluoro-α-[2-methyl-1-oxopropyl]-γ-oxo-N,β-diphenylbenzenebutaneamide mixture of [R-(R*,R*)], [R-(R*,S*)], [S-(R*,R*)] and [S-(R*,S*)] isomers, 540 L of heptanes and 60 L of toluene, 59 kg (400 mol) of 3-amino-1,1-diethoxypropane, and 22.3 kg (218 mol) of pivalic acid. The mixture is stirred and heated to reflux, removing water with a Dean Stark trap. The mixture is refluxed 32 hours and slowly cooled to 60°–65° C., diluted with 500 L of 2-propanol-water (3:2), seeded, and cooled to 20°–25° C. The product is isolated by filtration, washed with 300 L of 2-propanol, and dried in vacuo to yield 133.5 kg of 1-(3,3-diethoxypropyl)-5-(4-fluorophenyl)-2-(1-methylethyl)-N,4-diphenyl-1H-pyrrole-3-carboxamide; mp 125.1°–127.7° C. after recrystallization from ethanol.

HPLC: (acetonitrile:tetrahydrofuran:water) (40:25:55) 1.5 mL/min 254 nm Econosil $C_{18}$ 5 μ 25 cm R.T.=37.70 min 99.4% (area)

NMR: $((CD_3)_2CO)$ δ1.04 (6H, m, t), 1.47 (6H, d), 1.82 (2H, m), 3.40 (5H, m), 3.99 (2H, m), 4.43 (1H, brt), 6.90–7.50 (14H, m), 8.26 (1H, brs)

In a process analogous to Step C using appropriate starting materials, the following compounds of Formula XVI are prepared:

1-(3,3-Dimethoxypropyl)-5-(4-fluorophenyl)-2-(1-methylethyl)-N,4-diphenyl-1H-pyrrole-3-carboxamide; mp 167°–168.2° C.

5-(4-Fluorophenyl)-1-[2-(4-methyl-1,3-dioxolan-2-yl)ethyl-2-(1-methylethyl)-N,4-diphenyl-1H-pyrrole-3-carboxamide; bp 141.5°–145.9° C.

Step D: Preparation of 5-(4-Fluorophenyl)-2-(1-methylethyl)-1-(3-oxopropyl)-N,4-diphenyl-1H-pyrrole-3-carboxamide.

To a nitrogen purged flask fitted with an overhead stirrer, a thermometer, and a condenser is added 20 kg (37.8 mol) of 1-(3,3-diethoxypropyl)-5-(4-fluorophenyl)-2-(1-methylethyl)-N,4-diphenyl- 1H-pyrrole-3-carboxamide along with 200 L of acetone. The solution is stirred and 100 L of 2N hydrochloric acid solution is added. The mixture is heated to reflux for four hours then cooled to 50° C. ±5° C., seeded, and cooled to 0° C. ±5° C. The product is collected by filtration, washed with 100 L 2-propanol-water (1:1) and dried in vacuo at 50° C. for 64 hours to yield 16.2 kg of 5-(4-fluorophenyl)-2-(1-methylethyl)-1-(3-oxopropyl)-N,4-diphenyl-1H-pyrrole-3-carboxamide as an off-white solid.

Step E: Preparation of 2-(4-Fluorophenyl)-δ-hydroxy-5-(1-methylethyl)-β-oxo-3-phenyl-4-[(phenylamino)carbonyl]-1H-pyrrole-1-heptanoic acid, methyl ester.

A 22-L three-necked flask fitted with an overhead stirrer, a low temperature thermometer, and a 2-L calibrated addition funnel is dried with a nitrogen purge and 78 g (1.95 mol) 60% sodium hydride in mineral oil is added, followed by 248 mL (1.76 mol) diisopropylamine and 8 L tetrahydrofuran. The reaction is cooled to −10° to 0° C., a significant nitrogen purge was introduced through the flask, and 212 mL (1.92 mol) methyl acetoacetate is added in a slow stream over a 10 to 30-minute period. Stirring is continued at −10° to 10° C. for an additional 10 to 30 minutes. After cooling to −15° to −5° C., 2.2 L of 1.6M n-butyllithium in hexanes in added over a 30 to 60-minute period while maintaining the temperature below 0° C. Stirring is continued for an additional 1 to 1.5 hours at −15° to 0° C. and the mixture cooled to −35° to −15° C.

In a separate 5-L flask, 0.7 kg (1.54 mol) 5-(4-fluorophenyl)-2-(1-methylethyl)-1-(3-oxopropyl)-N, 4-diphenyl-1H-pyrrole-3-carboxamide is dissolved with 2.0 L of dry tetrahydrofuran, cooled to 0° to −5° C., and added to the anion solution over a 30 to 45 minute period. The reaction is stirred at −20° to −15° C. for 30 to 45 minutes, then quenched by the addition of 4 L aqueous 2N hydrochloric acid solution over 5 to 15 seconds while stirring rapidly. After stopping the agitation, the lower layer is separated and the remaining organic layer washed with 4 L saturated aqueous sodium chloride.

Step F: Preparation of cis-(4-Fluorophenyl)-β,δ-dihydroxy-5-(1-methylethyl)-3-phenyl-4-[(phenylamino)carbonyl]-1H-pyrrole-1-heptanoic acid, methyl ester.

The reaction solution obtained from Step E contained in a 50-L jacketed glass still is concentrated by vacuum distillation to a thick oil, then dissolved with 19 L tetrahydrofuran and cooled to 0° C. under an air atmosphere. Triethylborane, a 1 molar solution in hexanes, (3.20 L, 1.4 equivalents based on Step E) is added over a 10 minute period, the atmosphere on the flask is switched to nitrogen, and the flask cooled to −105° C. over 3.5 hours. During this period two liters of methanol are added when the temperature reaches −67° C. Powdered sodium borohydride (184 g, 4.8 mol) is added in 20 to 50-g portions over 1.5 hours, and the reaction maintained between −95° and −106° C. for 13 hours, then between −60° and −100° C. for 10 hours. Unreacted sodium borohydride is quenched by the addition of 750 mL (12.7 mol) acetic acid in 50-mL portions over a 45 minute period with a substantial amount of gas evolution and with a temperature rise from −60° to −40° C. Further quenching is accomplished by the addition of a solution of 1.0 L 30% hydrogen peroxide (9.7 mol), 3.0 L water, and 100 g dihydrogen sodium phosphate over a 15 minute period and is accompanied by a temperature rise from −40° to 0° C. The reaction is allowed to warm to room temperature overnight, then the lower layer separated off and the upper layer washed with 4.0 L of saturated aqueous sodium chloride solution.

Variation of Step F: Preparation of cis-2-(4-Fluorophenyl)-β,δ-dihydroxy-5-(1-methylethyl)-3-phenyl-4-(phenylamino)carbonyl-1H-pyrrole-1-heptanoic acid, methyl ester.

The reaction solution obtained from Step E is concentrated under vacuum to a volume of 5 to 8 L, then dissolved in 20 L tetrahydrofuran and 4 L methanol under a nitrogen atmosphere. This solution is cooled to −85° C. and 2.1 L of a 15% solution of methoxydiethylborane in tetrahydrofuran (2.1 mol, 1.0 equivalent based on Step E) is added. The reaction is cooled to −97° C. over one hour and 144 g (3.78 mol) of sodium borohydride added in 20 to 50-g portions over 1.5 hours. The reaction is maintained between −93° and −97° C. for 13 hours and allowed to warm to room temperature and stand for 60 hours under a nitrogen atmosphere.

The reaction is quenched by the addition of 460 mL (7.9 mol) acetic acid and concentrated by vacuum distillation to an oil. The residue is dissolved with 8 L methanol, concentrated by vacuum distillation, redissolved with 8 L methanol, and reconcentrated by vacuum distillation to a volume of 6 L. The solution is diluted with 8 L tetrahydrofuran, 4 L hexanes, and carried into the next step.

Step G: Preparation of trans-(±)-5-(4-Fluorophenyl)-2-(1-methylethyl)-N,4-diphenyl-1-[2-(tetrahydro-4-hydroxy-6-oxo-2H-pyran-2-yl)ethyl]-1H-pyrrole-3-carboxamide.

The crude reaction mixture of Step F is cooled to 8° C., 8.0 L of 2.0N aqueous sodium hydroxide is added, and the reaction stirred for 2 hours at 15° to 18° C. The reaction is diluted with 12 L water and the upper layer removed. The remaining aqueous layer is washed with 8 L hexanes then 8 L ethyl acetate is added followed by 1 L concentrated aqueous hydrochloric acid solution. The well-stirred mixture is allowed to separate, the lower layer discarded, and the upper layer washed four times with 4 L each of 2N aqueous hydrochloric acid solution.

The ethyl acetate layer is concentrated to a foamy syrup by vacuum distillation, and the residue dissolved in 8 L toluene. The toluene is concentrated by vacuum distillation to a volume of 6 L, then allowed to stand at room temperature for 16 hours. The resulting thick slurry is filtered on a Buchner funnel, washed with 1 L of cool toluene, washed with 2 L of hexanes, and dried in a vacuum oven for 24 hours at room temperature, resulting in 686 g of trans-(±)-5-(4-fluorophenyl)-2-(1-methylethyl)-N,4-diphenyl-1-[2-(tetrahydro-4-hydroxy-6-oxo-2H-pyran-2-yl)ethyl)-1H-pyrrole-3-carboxamide. The filtrates are washed with 2N aqueous hydrochloric acid solution and concentrated in vacuo to a volume of 2 L, then allowed to stand at room temperature for three days. The resulting solid is filtered, washed, and dried as before, resulting in 157 g of trans-(±)-5-(4-fluorophenyl)-2-(1-methylethyl)-N,4-diphenyl-1-[2-(tetrahydro-4-hydroxy-6-oxo-2H-pyran-2-yl)ethyl)-1H-pyrrole-3-carboxamide. HPLC of the solids indicates 95% trans with 1.3% cis lactone for the first crop and 95% trans with 2.3% cis lactone for the second crop. The two crops of solid are dissolved in 8 L ethyl acetate by heating to 50° to 60° C., then filtered through a Buchner funnel along with 8 L of hexanes which has been warmed to 50° C. The solution is allowed to cool to room temperature over 16 hours, the resulting slurry filtered through a Buchner funnel, and the solid washed with 2 L hexanes. The resulting solid is dried in a vacuum oven for 24 hours at room temperature, resulting in 720 g of trans-(±)-5-(4-fluorophenyl)-2-(1-methylethyl)-N,4-diphenyl-1-[2-(tetrahydro-4-hydroxy-6-oxo-2H-pyran-2-yl)ethyl]-1H-pyrrole-3-carboxamide with a 98%:0.9% trans:cis HPLC assay. The second crop obtained by concentration as before is approximately 100 g.

METHOD B

Step A: Preparation of (±)-cis-6-(2-aminoethyl)-2,2-dimethyl-1,3-dioxane-4-acetic acid.

A solution of 1.04 g (4.88 mmol) of (±)-cis-6-(cyanomethyl)-2,2-dimethyl-1,3-dioxane-4-acetic acid in 100 mL of methanol saturated with anhydrous ammonia is added to a Parr shaker bottle containing 0.53 g of water wet Raney nickel #30. The solution is heated at 45° C. and 50 psig hydrogen pressure for 17 hours. The suspension is cooled and filtered to remove the Raney nickel through filter aid and the precipitate washed with methanol. The filtrate is concentrated at reduced pressure. The residue is dissolved in methanol saturated with anhydrous ammonia treated with decolorizing charcoal, filtered through filter aid and evaporated to give 0.56 g of (±)-cis-6-(2-aminoethyl)-2,2-dimethyl-1,3-dioxane-4-acetic acid, mp 165° with decomposition at 169° C.

Fourier Transform Infrared (FTIR) (KBr): 1201.1, 1399.2, 1561.2, 2924.4, 3569.9 cm$^{-1}$.

$^1$H-NMR (D$_2$O, 200 MHz) δ0.84 (m, 1H), 0.96 (s, 3H), 1.11 (s, 3H), 1.2–1.5 (m, 3H), 1.84 (dd, 1H, J=14.0 Hz, J=6.6 Hz), 1.99 (dd, 1H, J=14.0 Hz, J=6.8 Hz), 2.68 (t, 2H, J=7.2 Hz), 3.6–3.85 (m, 1H), 3.85–4.15 (m, 1H).

$^{13}$C-NMR (D$_2$O, 50 MHz) δ19.64, 29.32, 32.94, 35.86, 36.95, 44.73, 68.16, 68.25, 100.18, 178.56.

Mass Spectrum (GC/MS), m/z 202, 198, 173, 142, 138, 120, 97, 82, 59, 43.

Step B: Preparation of Trans-(±)-5-(4-fluorophenyl)-2-(1-methylethyl)-N,4-diphenyl-1-[2-(tetrahydro-4-hydroxy-6-oxo-2H-pyran-2-yl)ethyl]-1H-pyrrole-3-carboxamide.

A solution of 0.26 g (1.21 mmol) of (±)-cis-6-(2-aminoethyl)-2,2-dimethyl-1,3-dioxane-4-acetic acid and 0.504 g (1.20 mmol) of (±)4-fluoro-α-[2-methyl-1-oxopropyl]-γ-oxo-N,β-diphenylbenzenebutaneamide mixture of [R-(R*,R*)], [R-(R*,S*)], [S-(R*,R*)] and [S-(R*,S*)] isomers in 5 mL of dimethyl sulfoxide is heated at 105° C. for 15 hours. The solution is cooled and poured into 100 mL of diethyl ether and 50 mL of saturated ammonium chloride in water. The layers are separated and the organic layer washed with water (2×50 mL) and 5% sodium hydroxide solution (2×100 mL—to extract the intermediate from unreacted diketone). The aqueous layer is acidified with dilute hydrochloric acid solution and extracted with 30 mL of ethyl acetate. A drop of concentrated hydrochloric acid is added to the ethyl acetate solution and allowed to stand 18 hours. The solution is concentrated in vacuo and the concentrate is redissolved in 30 mL of ethyl acetate and treated with one drop of concentrated hydrochloric acid. The solution is stirred two hours, concentrated in vacuo, and dissolved in 6 mL of toluene. Trans-(±)-5-(4-fluorophenyl)-2-(1-methylethyl)-N,4-diphenyl-1-[2-(tetrahydro-4-hydroxy-6-oxo-2H-pyran-2-yl)ethyl]-1H-pyrrole-3-carboxamide crystallizes and is isolated by filtration. A total of 0.16 g of trans-(±)-5-(4-fluorophenyl)-2-(1-methylethyl)-N,4-diphenyl-1-[2-(tetrahydro-4-hydroxy-6-oxo-2H-pyran-2-yl)ethyl]-1H-pyrrole-3-carboxamide is isolated in two crops.

METHOD C

Step A: Preparation of either (±)-(2α,4β,6β) or (±)-(2α,4α,6β)-2-phenyl-6-(2-propenyl)-1,3-dioxane-4-acetonitrile.

Potassium cyanide, 1.3 g (20 mmol), is added to a room temperature solution of (R*,R*)-α-2-propenyloxiraneethanol, 2.56 g (20 mmol), in 25 mL of 4:1 isopropanol:water. The solution is stirred for 20 hours at ambient temperature, concentrated, and partitioned between ethyl acetate and brine. The aqueous layer is extracted 2× with ethyl acetate and the combined ethyl acetate extracts are washed with brine and dried (magnesium sulfate). The crude product is dissolved in 20 mL of benzaldehyde dimethyl acetal, camphorsulfonic acid is added, and the solution is stirred for 18 hours at room temperature. Concentration and flash chromatography after concentration in vacuo provides 1.30 g of either $(\pm)$-$(2\alpha,4\beta,6\beta)$ or $(\pm)$-$(2\alpha,4\alpha,6\beta)$-2-phenyl-6-(2-propenyl)-1,3-dioxane-4-acetonitrile δMHz NMR (CDCl$_3$) δ1.48 (m, 1H), 1.71 (m, 1H), 2.41 (m, 2H), 2.58 (m, 2H), 3.87 (m, 1H), 4.03 (m, 1H), 5.1-5.2 (m, 2H), 5.53 (s, 1H), 5.87 (m, 1H), 7.3-7.6 (m, 5H)

$^{13}$C-NMR (CDCl$_3$, 50 MHz) δ24.23, 35.07, 39.79, 71.57, 75.48, 100.44, 116.37, 117.53, 125.89, 127.91, 128.61, 133.05, 137.71.

GC/MS m/e 243 (M+), 242, 203, 202, 120, 107, 105, 79, 75, 41.

FTIR (neat) 699.6, 758.7, 920.8, 1028.8, 1051.9, 1121.4, 1345.2, 1383.7, 1401.7, 2253.1, 2916.6 cm$^{-1}$.

Step B: Preparation of either $(\pm)$-$(2\alpha,4\alpha,6\alpha)$ or $(\pm)$-$(2\alpha,4\beta,6\beta)$-6-(2-oxoethyl)-2-phenyl-1,3-dioxane-4-acetonitrile.

A solution of either $(\pm)$-$(2\alpha,4\beta,6\beta)$ or $(\pm)$-$(2\alpha,4\alpha,6\alpha)$-2-phenyl-6-(2-propenyl)-1,3-dioxane-4-acetonitrile, 4.11 g (16.89 mmol), in 100 mL of dichloromethane is cooled to $-78°$ C. under nitrogen. Ozone (Welsbach generator, flow rate 0.1, voltage=90 V) is then passed through a fritted gas inlet tube into the solution until the blue color of ozone appears. The current is turned off, and oxygen bubbled through until the blue color is discharged. Triphenylphosphine, 4.87 g (18.58 mmol), is added and the colorless solution is allowed to warm to room temperature. Flash chromatography provides after concentration in vacuo 3.75 g of pure either $(\pm)$-$(2\alpha,4\alpha,6\alpha)$ or $(\pm)$-$(2\alpha,4\beta,6\beta)$-6-(2-oxoethyl)-2-phenyl-1,3-dioxane-4-acetonitrile.

GC/MS m/e 245 (M+), 244, 123, 105, 95, 94, 77, 51, 41.

Step C: Preparation of either $(\pm)$-$(2\alpha,4\alpha,6\alpha)$ or $(\pm)$-$(2\alpha,4\beta,6\beta)$-6-(cyanomethyl)-2-phenyl-1,3-dioxane-4-acetic acid.

Jones reagent (chromium trioxide-sulfuric acid-water), 3.8 mL (97.6 mmol), is added dropwise to a 0° C. solution of either $(\pm)$-$(2\alpha,4\alpha,6\alpha)$ or $(\pm)$-$(2\alpha,4\beta,6\beta)$-6-(2-oxoethyl)-2-phenyl-1,3-dioxane-4-acetonitrile, 1.86 g (7.6 mmol), dissolved in 50 mL of acetone until the orange color is not discharged. After stirring a further 15 minutes, the mixture is poured into 300 mL of diethyl ether and washed with brine until the aqueous washes are colorless. The diethyl ether layer is dried (magnesium sulfate), filtered, and concentrated to provide 1.84 g of either $(\pm)$-$(2\alpha,4\alpha,6\alpha)$ or $(\pm)$-$(2\alpha,4\beta,6\beta)$-6-(cyanomethyl)-2-phenyl-1,3-dioxane-4-acetic acid as a yellow gum.

200 MHz NMR (CDCl$_3$) δ1.61 (m, 1H), 2.04 (m, 1H), 2.6-2.8 (m, 3H), 2.82 (dd, 1H, J=15.9 Hz, J=7.1 Hz), 4.20 (m, 1H), 4.40 (m, 1H), 5.60 (s, 1H), 7.2-7.5 (m, 5H).

Step D: Preparation of either $(\pm)$-$(2\alpha,4\alpha,6\alpha)$ or $(\pm)$-$(2\alpha,4\beta,6\beta)$-6-(2-aminoethyl)-2-phenyl-1,3-dioxane-4-acetic acid.

A solution of 0.16 g (0.61 mmol) of either $(\pm)$-$(2\alpha,4\alpha,6\alpha)$ or $(\pm)$-$(2\alpha,4\beta,6\beta)$-6-(cyanomethyl)-2-phenyl-1,3-dioxane-4-acetic acid in 50 mL of methanol saturated with anhydrous ammonia is added to a Parr shaker bottle containing 0.2 g of water wet Raney nickel #30. The solution is heated at 40° C. and 50 pounds per square inch gage (psig) hydrogen pressure for 6 hours. The suspension is cooled and filtered to remove the Raney nickel through filter aid and the precipitate washed with methanol. The filtrate is concentrated at reduced pressure. The residue is dissolved in methanol saturated with anhydrous ammonia treated with decolorizing charcoal, filtered through filter aid and evaporated to give 0.11 g of either $(\pm)$-$(2\alpha,4\alpha,6\alpha)$ or $(\pm)$-$(2\alpha,4\beta,6\beta)$-6-(2-aminoethyl)-2-phenyl-1,3-dioxane-4-acetic acid; mp 215.9°-217.9° C. with decomposition.

200 MHz NMR (D$_2$O) δ1.4-1.9 (m, 4H), 2.39 (dd, 1H, J =14.8 Hz, J=6.7 Hz), 2.55 (dd, 1H, J=14.8 Hz, J=7.4 Hz), 2.73 (t, 2H, J=7.2 Hz) 4.11 (m, 1H), 4.33 (m, 1H), 5.70 (s, 1H), 7.4-7.6 (m, 5H).

$^{13}$C-NMR (D$_2$O, 50 MHz) δ39.20, 39.78, 40.83, 47.11, 78.34, 78.73, 104.06, 129.15, 131.56, 132.38, 140.51, 181.89.

Step E: Preparation of Trans-$(\pm)$-5-(4-fluorophenyl)-2-(1-methylethyl)-N,4-diphenyl-1-[2-(tetrahydro-4-hydroxy-6-oxo-2H-pyran-2-yl)ethyl]-1H-pyrrole-3-carboxamide.

A solution of 0.31 g (1.21 mmol) of either $(\pm)$-$(2\alpha,4\alpha,6\alpha)$ or $(\pm)$-$(2\alpha,4\beta,6\beta)$-6-(2-aminoethyl)-2-phenyl-1,3-dioxane-4-acetic acid and 0.504 g (1.20 mmol) of $(\pm)$-4-fluoro-α-[2-methyl-1-oxopropyl]-γ-oxo-N,β-diphenylbenzenebutaneamide mixture of [R-(R*,R*)], [R-(R*,S*)], [S-(R*,R*)] and [S-(R*,S*)] isomers in 5 mL of dimethyl sulfoxide is heated at 105° C. for 15 hours. The solution is cooled and poured into 100 mL of diethyl ether and 50 mL of saturated ammonium chloride in water. The layers are separated and the organic layer washed with water (2×50 mL) and 5% sodium hydroxide solution (2×100 mL—to extract the intermediate from unreacted diketone). The aqueous layer is acidified with dilute hydrochloric acid solution, stirred for three hours and extracted with 30 mL of ethyl acetate. A drop of concentrated hydrochloric acid is added to the ethyl acetate solution, the solution is stirred and allowed to stand 18 hours. The solution is concentrated in vacuo and the concentrate is redissolved in 30 mL of ethyl acetate and treated with one drop of concentrated hydrochloric acid. The solution is stirred two hours, concentrated in vacuo, and dissolved in 6 mL of toluene. Trans-$(\pm)$-5-(4-fluorophenyl)-2-(1-methylethyl)-N,4-diphenyl-1-[2-(tetrahydro-4-hydroxy-6-oxo-2H-pyran-2-yl)ethyl]-1H-pyrrole-3-carboxamide crystallizes and is isolated by filtration. A total of 0.16 g of trans-$(\pm)$-5-(4-fluorophenyl)-2-(1-methylethyl)-N,4-diphenyl-1-[2-(tetrahydro-4-hydroxy-6-oxo-2H-pyran-2-yl)ethyl]-1H-pyrrole-3-carboxamide is isolated in two crops.

METHOD D

Step A: Preparation of $(\pm)$-cis-9-(2-propenyl)-6,10-dioxaspiro[4.5]decane-7-acetonitrile.

Potassium cyanide, 1.3 g (20 mmol), is added to a room temperature solution of (R*,R*)-α-2-propenyloxiraneethanol, 2.56 g (20 mmol), in 25 mL of 4:1 isopropanol:water. The solution is stirred for 20 hours at ambient temperature, concentrated, and partitioned between ethyl acetate and brine. The aqueous layer is extracted 2× with ethyl acetate and the combined ethyl acetate extracts are washed with brine and dried (magnesium sulfate). The crude product is dissolved in 20 mL of 1,1-dimethoxycyclopentane, camphorsulfonic acid is added, and the solution is stirred for 18 hours at room temperature. Concentration and flash chromatography after concentration in vacuo provides 1.40 g of (±)-cis-9-(2-propenyl)-6,10-dioxaspiro[4.5]-decane-7-acetonitrile.

Step B: Preparation of (±)-cis-9-(2-oxoethyl)-6,10-dioxaspiro[4.5]decane-7-acetonitrile.

A solution of (±)-cis-9-(2-propenyl)-6,10-dioxaspiro[4.5]decane-7-acetonitrile, 3.4 g (15.36 mmol), in 100 mL of dichloromethane is cooled to −78° C. under nitrogen. Ozone (Welsbach generator, flow rate 0.1, voltage=90 V) is then passed through a fritted gas inlet tube into the solution until the blue color of ozone appears. The current is turned off, and oxygen bubbled through until the blue color is discharged. Triphenylphosphine, 4.2 g (16 mmol), is added and the colorless solution is allowed to warm to room temperature. Flash chromatography provides after concentration in vacuo 2.5 g of pure (±)-cis-9-(2-oxoethyl)-6,10-dioxaspiro[4.5]decane-7-acetic acid.

Jones reagent (chromium trioxide-sulfuric acid-water), 3.8 mL (97.6 mmol), is added dropwise to a 0° C. solution of (±)-cis-9-(2-oxoethyl)-6-10-dioxaspiro[4.5]decane-2-acetonitrile 1.70 (7.6 mmol), dissolved in 50 mL of acetone until the orange color is not discharged. After stirring a further 15 minutes, the mixture is poured into 300 mL of diethyl ether and washed with brine until the aqueous washes are colorless. The diethyl ether layer is dried (magnesium sulfate), filtered, and concentrated to provide 1.20 g of (±)-cis-9-(cyanomethyl)-6,10-dioxaspiro[4.5]decane-7-acetic acid as a colorless solid.

Step D: Preparation of (±)-cis-9-(2-aminoethyl)-6,10-dioxaspiro[4.5]decane-7-acetic acid.

A solution of 1.17 g (4.88 mmol) of (±)-cis-9-(cyanomethyl)-6,10-dioxaspiro[4.5]decane-7-acetic acid in 100 mL of methanol saturated with anhydrous ammonia is added to a Parr shaker bottle containing 0.53 g of water wet Raney nickel #30. The solution is heated at 45° C. and 50 pounds per square inch gage (psig) hydrogen pressure for 17 hours. The suspension is cooled and filtered to remove the Raney nickel through filter aid and the precipitate is washed with methanol. The filtrate is concentrated at reduced pressure. The residue is dissolved in methanol saturated with anhydrous ammonia treated with decolorizing charcoal, filtered through filter aid and evaporated to give 0.56 g of (±)-cis-9-(2-aminoethyl)-6,10-dioxaspiro[4.5]decane-7-acetic acid.

Step E: Preparation of Trans-(±)-5-(4-fluorophenyl)-2-(1-methylethyl)-N,4-diphenyl-1-[2-(tetrahydro-4-hydroxy-6-oxo-2H-pyran-2-yl)ethyl]-1H-pyrrole-3-carboxamide.

A solution of 0.295 g (1.21 mmol) of (±)-cis-9-(2-aminoethyl)-6,10-dioxaspiro[4.5]decane-7-acetic acid and 0.504 g (1.20 mmol) of (±)-4-fluoro-α-[2-methyl-1-oxopropyl]-γ-oxo-N,β-diphenylbenzenebutaneamide mixture of [R-(R*,R*)], [R-(R*,S*)], [S-(R*,R*)] and [S-(R*,S*)] isomers in 5 mL of dimethyl sulfoxide is heated at 105° C. for 15 hours. The solution is cooled and poured into 100 mL of diethyl ether and 50 mL of saturated ammonium chloride in water. The layers are separated and the organic layer washed with water (2×50 mL) and 5% sodium hydroxide solution (2×100 mL—to extract the intermediate protected acid from unreacted diketone). The aqueous layer is acidified with dilute hydrochloric acid solution, stirred for three hours and extracted with 30 mL of ethyl acetate. A drop of concentrated hydrochloric acid is added to the ethyl acetate solution and allowed to stand 18 hours. The solution is concentrated in vacuo and the concentrate is redissolved in 30 mL of ethyl acetate and treated with one drop of concentrated hydrochloric acid. The solution is stirred two hours, concentrated in vacuo, and dissolved in 6 mL of toluene. Trans-(±)-5-(4-fluorophenyl)-2-(1-methylethyl)-N,4-diphenyl-1-[2-(tetrahydro-4-hydroxy-6-oxo-2H-pyran-2-yl)ethyl]-1H-pyrrole-3-carboxamide crystallizes and is isolated by filtration. A total of 0.16 g of trans-(±)-5-(4-fluorophenyl)-2-(1-methylethyl)-N,4-diphenyl-1-[2-(tetrahydro-4-hydroxy-6-oxo-2H-pyran-2-yl)ethyl]-1H-pyrrole-3-carboxamide is isolated in two crops.

METHOD E

Step A: Preparation of (±)-cis-4-(2-propenyl)-1,5-dioxaspiro[5.5]undecane-2-acetonitrile.

Potassium cyanide, 1.3 g (20 mmol), is added to a room temperature solution of (R*,R*)-α-2-propenyloxiraneethanol, 2.56 g (20 mmol), in 25 mL of 4:1 isopropanol:water. The solution is stirred for 20 hours at ambient temperature, concentrated, and partitioned between ethyl acetate and brine. The aqueous layer is extracted 2× with ethyl acetate and the combined ethyl acetate extracts are washed with brine and dried (magnesium sulfate). The crude product is dissolved in 20 mL of 2,2-dimethoxycyclohexane, camphorsulfonic acid is added, and the solution is stirred for 18 hours at room temperature. Concentration in vacuo provides 1.50 g of (±)-cis-4-(2-propenyl)-1,5-dioxaspiro[5.5]undecane-2-acetonitrile 200 MHz NMR (CDCl$_3$) δ1.26 (m, 1H), 1.4–1.7 (m, 8H), 1.87 (m, 2H), 2.1–2.3 (m, 2H), 2.51 (d, 2H, J=6.05 Hz), 3.95 (m, 1H), 4.15 (m, 1H), 5.0–5.2 (m, 2H), 5.83 (m, 1H).

$^{13}$C-NMR (CDCl$_3$, 50 MHz) δ22.16, 24.71, 25.42, 28.20, 35.47, 38.33, 40.30, 64.08, 66.87, 98.84, 116.53, 116.83, 113.46.

GC/MS m/e 235 (m+), 206, 192, 120, 99, 93, 79, 69, 55, 41.

FTIR (film) 964.5, 1121.4, 1160.0, 2253.1, 2937.2 cm$^{-1}$.

Step B: Preparation of (±)-cis-4-(2-oxoethyl)-1,5-dioxaspiro[5.5]undecane-2-acetonitrile.

A solution of (±)-cis-4-(2-propenyl)-1,5-dioxaspiro[5.5]undecane-2-acetonitrile 4.26 g (19.42 mmol), in 100 mL of dichloromethane is cooled to −78° C. under nitrogen. Ozone (Welsbach generator, flow rate 0.1, voltage=90 V) is then passed through a fritted gas inlet tube into the solution until the blue color of ozone appears. The current is turned off, and oxygen bubbled through until the blue color is discharged. Triphenylphosphine, 5.6 g (21.36 mmol), is added and the colorless solution is allowed to warm to room temperature. Flash chromatography provides after concentration in vacuo 4.04 g of pure (±)-cis-4-(2-oxoethyl)-1,5-dioxaspiro[5.5]undecane-2-acetonitrile.

200 MHz NMR (CDCl$_3$) δ1.3–2.0 (m, 12H), 2.5–2.7 (m, 4H), 4.20 (m, 1H), 4.36 (m, 1H), 9.81 (t, 1H, J=1.74 Hz).

$^{13}$C-NMR (CDCl$_3$, 50 MHz) δ22.39, 22.44, 24.97, 25.59, 28.44, 35.82, 38.48, 49.54, 63.25, 64.17, 99.66, 116.57, 199.82.

GC/MS m/e 237 (m+), 208, 194, 122, 94, 81, 55, 42, 41.

FTIR (film) 969.6, 1069.9, 1126.5, 1160.0, 1368.3, 1386.3, 1728.4, 2934.6 cm$^{-1}$.

Step C: Preparation of
(±)-cis-4-(cyanomethyl)-1,5-dioxaspiro[5.5]undecane-2-acetic acid.

Jones reagent (chromium trioxide-sulfuric acid-water), 4.4 mL (8.85 mmol), is added dropwise to a 0° C. solution of (±)-cis-4-(2-oxoethyl)-1,5-dioxaspiro[5.5]undecane-2-acetonitrile, 3.62 g (12.6 mmol), dissolved in 30 mL of acetone until the orange color is not discharged. After stirring a further 15 minutes, the mixture is poured into 300 mL of diethyl ether and washed with brine until the aqueous washes are colorless. The diethyl ether layer is dried (magnesium sulfate), filtered, and concentrated to provide 3.65 g of (±)-cis-4-(cyanomethyl)-1,5-dioxaspiro[5.5]undecane-2-acetic acid as a yellow solid.

200 MHz NMR (Pyridine) δ1.2–2.0 (m, 12H), 2.5–2.9 (m, 4H), 4.19 (m, 1H), 4.50 (m, 1H).

Step D: Preparation of
(±)-cis-4-(2-aminoethyl)-1,5-dioxaspiro[5.5]undecane-2-acetic acid.

A solution of 0.13 g of (±)-cis-4-(cyanomethyl)-1,5-dioxaspiro[5.5]undecane-2-acetic acid in 20 mL of methanol saturated with anhydrous ammonia is added to a Parr shaker bottle containing 0.2 g of water wet Raney nickel #30. The solution is heated at 40° C. and 50 pounds per square inch gage (psig) hydrogen pressure for 17 hours. The suspension is cooled and filtered to remove the Raney nickel through filter aid and the precipitate is washed with methanol. The filtrate is concentrated at reduced pressure. The residue is dissolved in methanol saturated with anhydrous ammonia, treated with decolorizing charcoal, filtered through filter aid and evaporated to give 0.13 g of (±)-cis-4-(2-aminoethyl)-1,5-dioxaspiro[5.5]undecane-2-acetic acid.

200 MHz NMR (D$_2$O) δ1.1–1.7 (m, 10H), 1.75–2.1 (m, 4H), 2.19 (dd, 1H, J=14.6 Hz, J=6.7 Hz), 2.31 (dd, 1H, J=14.6 Hz, J=7.3 Hz), 2.69 (t, 2H, J=7.1 Hz), 4.09 (m, 1H), 4.34 (m, 1H).

$^{13}$C-NMR (D$_2$O, 50 MHz) δ24.50, 24.73, 27.55, 30.80, 38.91, 39.39, 39.63, 40.48, 47.03, 69.37, 69.54, 102.74, 181.33.

Step E: Preparation of
Trans-(±)-5-(4-fluorophenyl)-2-(1-methylethyl)-N,4-diphenyl-1-[2-(tetrahydro-4-hydroxy-6-oxo-2H-pyran-2-yl)ethyl]-1H-pyrrole-3-carboxamide.

A solution of 0.31 g (1.21 mmol) of (±)-cis-4-(2-aminoethyl)-1,5-dioxaspiro[5.5]undecane-2-acetic acid and 0.504 g (1.20 mmol) of (±)-4-fluoro-α-[2-methyl-1-oxopropyl]-γ-oxo-N,β-diphenylbenzenebutaneamide mixture of [R-(R*,R*)], [R-(R*,S*)], [S-(R*,R*)] and [S-(R*,S*)] isomers in 5 mL of dimethyl sulfoxide is heated at 105° C. for 15 hours. The solution is cooled and poured into 100 mL of diethyl ether and 50 mL of saturated ammonium chloride in water. The layers are separated and the organic layer washed with water (2×50 mL) and 5% sodium hydroxide solution (2×100 mL—to extract the intermediate acid from unreacted diketone). The aqueous layer is acidified with dilute hydrochloric acid solution, stirred for three hours and extracted with 30 mL of ethyl acetate to remove the protecting group before lactonization. The extract is concentrated and dissolved in 30 mL of ethyl acetate. A drop of concentrated hydrochloric acid is added to the ethyl acetate solution and allowed to stand 18 hours. The solution is concentrated in vacuo and the concentrate is redissolved in 30 mL of ethyl acetate and treated with one drop of concentrated hydrochloric acid. The solution is stirred two hours, concentrated in vacuo, and dissolved in 6 mL of toluene. Trans-(±)-5-(4-fluorophenyl)-2-(1-methylethyl)-N,4-diphenyl-1-[2-(tetrahydro-4-hydroxy-6-oxo-2H-pyran-2-yl)ethyl]-1H-pyrrole-3-carboxamide crystallizes and is isolated by filtration. A total of 0.155 g of trans-(±)-5-(4-fluorophenyl)-2-(1-methylethyl)-N,4-diphenyl-1-[2-(tetrahydro-4-hydroxy-6-oxo-2H-pyran-2yl)ethyl]-1H-pyrrole-3-carboxamide is isolated in two crops.

METHOD F

Step A: Preparation of
(±)-cis-6-(2-propenyl)-1,3-dioxane-4-acetonitrile

Potassium cyanide, 1.3 g (20 mmol), is added to a room temperature solution of (R*,R*)-α-2-propenyloxiraneethanol, 2.56 g (20 mmol), in 25 mL of 4:1 isopropanol:water. The solution is stirred for 20 hours at ambient temperature, concentrated, and partitioned between ethyl acetate and brine. The aqueous layer is extracted 2× with ethyl acetate and the combined ethyl acetate extracts are washed with brine and dried (magnesium sulfate). The crude product is dissolved in 20 mL of dimethoxymethane, camphorsulfonic acid is added, and the solution is stirred for 18 hours at room temperature. Concentration and flash chromatography after concentration in vacuo provides 1.20 g of (±)-cis-6-(2-propenyl)-1,3-dioxane-4-acetonitrile.

Step B: Preparation of
(±)-cis-6-(2-oxoethyl)-1,3-dioxane-4-acetonitrile.

A solution of (±)-cis-6-(2-propenyl)-1,3-dioxane-4-acetonitrile, 2.57 g (15.36 mmol), in 100 mL of dichloromethane is cooled to −78° C. under nitrogen. Ozone (Welsbach generator, flow rate 0.1, voltage=90 V) is then passed through a fritted gas inlet tube into the solution until the blue color of ozone appears. The current is turned off, and oxygen bubbled through until the blue color is discharged. Triphenylphosphine, 4.87 g (28.58 mmol), is added and the colorless solution is allowed to warm to room temperature. Flash chromatography provides after concentration in vacuo 2.3 g of pure (±)-cis-6-(2-oxoethyl)-1,3-dioxane-4-acetonitrile.

Step C: Preparation of
(±)-cis-6-(cyanomethyl)-1,3-dioxane-4-acetic acid.

Jones reagent (chromium trioxide-sulfuric acid-water), 3.8 mL (97.6 mmol), is added dropwise to a 0° C. solution of (±)-cis-6-(2-oxoethyl)-1,3-dioxane-4acetonitrile, 1.29 g (7.6 mmol), dissolved in 50 mL of acetone until the orange color is not discharged. After stirring a further 15 minutes, the mixture is poured into 300 mL of diethyl ether and washed with brine until the aqueous washes are colorless. The diethyl ether layer is dried (magnesium sulfate), filtered, and concentrated to provide 1.2 g of (±)-cis-6-(cyanomethyl)-1,3-dioxane-4-acetic acid as a colorless solid.

Step D: Preparation of (±)-cis-6-(2-aminoethyl)-1,3-dioxane-4-acetic acid.

A solution of 1.04 (4.88 mmol) of (±)-cis-6-(cyanomethyl)-1,3-dioxane-4-acetic acid in 100 mL of methanol saturated with anhydrous ammonia is added to a Parr shaker bottle containing 0.53 g of water wet Raney nickel #30. The solution is heated at 45° C. and 50 pounds per square inch gage (psig) hydrogen pressure for 17 hours. The suspension is cooled and filtered to remove the Raney nickel through filter aid and the precipitate washed with methanol. The filtrate is concentrated at reduced pressure. The residue is dissolve in methanol saturated with anhydrous ammonia, treated with decolorizing charcoal, filtered through filter aid and evaporated to give 0.56 g of (±)-cis-6-(2-aminoethyl)-1,3-dioxane-4-acetic acid.

Step E: Preparation of Trans-(±)-5-(4-fluorophenyl)-2-(1-methylethyl)-N,4-diphenyl-1-[2-(tetrahydro-4-hydroxy-6-oxo-2H-pyran-2-yl)ethyl]-1H-pyrrole-3-carboxamide.

A solution of 0.26 g (1.21 mmol) of (±)-cis-6-(2-aminoethyl)-1,3-dioxane-4acetic acid and 0.504 g (1.20 mmol) of (±)-4-fluoro-α-[2-methyl-1-oxopropyl]-γ-oxo-N,β-diphenylbenzenebutaneamide in 5 mL of dimethyl sulfoxide is heated at 105° C. for 15 hours. The solution is cooled and poured into 100 mL of diethyl ether and 50 mL of saturated ammonium chloride in water. The layers are separated and the organic layer washed with water (2×50 mL) and 5% sodium hydroxide solution (2×100 mL—to extract the intermediate acid from unreacted diketone). The aqueous layer is acidified with dilute hydrochloric acid solution and extracted with 30 mL of ethyl acetate. A drop of concentrated hydrochloric acid is added to the ethyl acetate solution and allowed to stand 18 hours. The solution is concentrated in vacuo and the concentrate is redissolved in 30 mL of ethyl acetate and treated with one drop of concentrated hydrochloric acid. The solution is stirred two hours. concentrated in vacuo, and dissolved in 6 mL of toluene. Trans-(±)-5-(4-fluorophenyl)-2-(1-methylethyl)-N,4-diphenyl-1-[2-(tetrahydro-4-hydroxy-6-oxo-2H-pyran-2-yl)ethyl]-1H-pyrrole-3-carboxamide crystallizes and is isolated by filtration. A total of 0.15 g of trans-(±)-5-(4-fluorophenyl)-2-(1-methylethyl)-N,4-diphenyl-1-[2-(tetrahydro-4-hydroxy-6-oxo-2H-pyran-2-yl)ethyl]-1H-pyrrole-3-carboxamide is isolated in two crops.

METHOD G

Step A: Preparation of either (±)-(2α,4β,6β) or (±)-(2α,4α,6α)-2-methyl-6-(2-propenyl)-1,3-dioxane-4-acetonitrile.

Potassium cyanide, 1.3 g (20 mmol), is added to a room temperature solution of (R*,R*)-α-2-propenyloxiraneethanol, 2.56 g (20 mmol), in 25 mL of 4:1 isopropanol:water. The solution is stirred for 20 hours at ambient temperature, concentrated, and partitioned between ethyl acetate and brine. The aqueous layer is extracted 2× with ethyl acetate and the combined ethyl acetate extracts are washed with brine and dried (magnesium sulfate). The crude product is dissolved in 20 mL of 1,1-dimethoxyethane, camphorsulfonic acid is added, and the solution is stirred for 18 hours at room temperature. Concentration and flash chromatography after concentration in vacuo provides 1.30 g of either (±)-(2α,4β,6β) or (±)-(2α,4α,6β)-2-methyl-6-(2-propenyl)-1,3-dioxane-4-acetonitrile.

Step B: Preparation of either (±)-(2α,4α,6α) or (±)-(2α,4β,6β)-2-methyl-6-(2-oxoethyl)-1,3-dioxane-4-acetonitrile.

A solution of either (±)-(2α,4β,6β) or (±)-(2α,4α,6α)-2-methyl-6-(2-propenyl)-1,3-dioxane-4-acetonitrile, 2.78 g (15.36 mmol), in 100 mL of dichloromethane is cooled to −78° C. under nitrogen. Ozone (Welsbach generator, flow rate 0.1, voltage=90 V) is then passed through a fritted gas inlet tube into the solution until the blue color of ozone appears. The current is turned off, and oxygen bubbled through until the blue color is discharged. Triphenylphosphine, 4.2 g (16 mmol), is added and the colorless solution is allowed to warm to room temperature. Flash chromatography provides after concentration in vacuo 2.5 g of pure either (±)-(2α,4α,6α) or (±)-(2α,4β,6β)-2-methyl-6-(2-oxoethyl)-1,3-dioxane-4-acetonitrile.

Step C: Preparation of either (±)-(2α,4α,6α) or (±)-(2α,4β,6β)-6-(cyanomethyl)-2-methyl-1,3-dioxane-4-acetic acid.

Jones reagent (chromium trioxide-sulfuric acid-water), 3.8 mL (7.6 mmol), is added dropwise to a 0° C. solution of either (±)-(2α,4α,6α) or (±)-(2α,4β,6β)-2-methyl-6-(2-oxoethyl)-1,3-dioxane-4-acetonitrile, 1.40 g (7.6 mmol), dissolved in 50 mL of acetone until the orange color is not discharged. After stirring a further 15 minutes, the mixture is poured into 300 mL of diethyl ether and washed with brine until the aqueous washes are colorless. The diethyl ether layer is dried (magnesium sulfate), filtered, and concentrated to provide 1.01 g of either (±)-(2α,4α,6α) or (±)-(2α,4β,6β)-6-(cyanomethyl)-2-methyl-1,3-dioxane-4-acetic acid as a colorless solid.

Step D: Preparation of either (±)-(2α,4α6α) or (±)-(2α,4β,6β)-6-(2-aminoethyl)-2-methyl-1,3-dioxane-4-acetic acid.

A solution of 0.97 g (4.88 mmol) of either (±)-(2α,4α,6α) or (±)-(2α,4β,6β)-6-(cyanomethyl)-2-methyl-1,3-dioxane-4-acetic acid in 100 mL of methanol saturated with anhydrous ammonia is added to a Parr shaker bottle containing 0.53 g of water wet Raney nickel #30. The solution is heated at 45° C. and 50 pounds per square inch gage (psig) hydrogen pressure for 17 hours. The suspension is cooled and filtered to remove the Raney nickel through filter aid and the precipitate washed with methanol. The filtrate is concentrated at reduced pressure. The residue is dissolved in methanol saturated with anhydrous ammonia treated with decolorizing charcoal, filtered through filter aid and evaporated to give 0.50 g of either (±)-(2α,4α,6α) or (±)-(2α,4β,6β)-6-(2-aminoethyl)-2-methyl-1,3-dioxane-4-acetic acid.

Step E: Preparation of Trans-(±)-5-(4-fluorophenyl)-2-(1-methylethyl)-N,4-diphenyl-1-[2-(tetrahydro-4-hydroxy-6-oxo-2H-pyran-2-yl)ethyl]-1H-pyrrole-3-carboxamide.

A solution of 0.31 g of either (±)-(2α,4α,6α) or (±)-(2α,4β,6β)-6-(2-aminoethyl)-2-methyl-1,3-dioxane-4-acetic acid and 0.504 g (1.20 mmol) of (±)-4-fluoro-α-[2-methyl-1-oxopropyl]-γ-oxo-N,β-diphenylbenzenebutaneamide in 5 mL of dimethyl sulfoxide is heated at 105° C. for 15 hours. The solution is cooled and poured into 100 mL of diethyl ether and 50 mL of saturated ammonium chloride in water. The layers are separated and the organic layer washed with water (2×50 mL) and 5% sodium hydroxide solution (2×100 mL—to extract the intermediate acid from unreacted diketone). The aqueous layer is acidified with dilute hydrochloric acid solution, stirred for three hours and extracted with 30 mL of ethyl acetate. A drop of concentrated hydrochloric acid is added to the ethyl acetate solution and allowed to stand 18 hours. The solution is concentrated in vacuo and the concentrate is redissolved in 30 mL of ethyl acetate and treated with one drop of concentrated hydrochloric acid. The solution is stirred two hours, concentrated in vacuo, and dissolved in 6 mL of toluene. Trans-($\pm$)-5-(4-fluorophenyl)-2-(1-methylethyl)-N,4-diphenyl-1-[2-(tetrahydro-4-hydroxy-6-oxo-2H-pyran-2-yl)ethyl]-1H-pyrrole-3-carboxamide crystallizes and is isolated by filtration. A total of 0.14 g of trans-($\pm$)-5-(4-fluorophenyl)-2-(1-methylethyl)-N,4-diphenyl-1-[2-(tetrahydro-4-hydroxy-6-oxo-2H-pyran-2-yl)ethyl]-1H-pyrrole-3-carboxamide is isolated in two crops.

METHOD H

Step A: Preparation of ($\pm$)-cis-1,1-dimethylethyl 6-(cyanomethyl)-2,2-dimethyl-1,3-dioxane-4-acetate.

($\pm$)-cis-6-(cyanomethyl)-2,2-dimethyl-1,3-dioxane-4-acetic acid (3.72 g, 17.44 mmol) is dissolved in 20 mL of dichloromethane, cooled to 0° C. and 0.2 g of 4-dimethylaminopyridine (DMAP) is added, followed by t-butyl alcohol and followed by 4.32 g of dicyclohexylcarbodiimide (DCC). This solution is allowed to slowly warm to room temperature over a 76.5-hour period. Thin layer chromotography (TLC) shows mainly product, and some slightly lower Rf by-products. The mixture is stirred one hour and 50 mL of dichloromethane is added and stirring continues five hours. An additional 100 mL of diethyl ether is added and the mixture filtered. The precipitate is washed with diethyl ether. The filtrate is concentrated to an oil. The crude product is chromatographed on silica gel eluting with 4:1 hexane:ethyl acetate. The eluate is concentrated to yield ($\pm$)-cis-1,1-dimethylethyl 6-(cyanomethyl)-b 2,2-dimethyl-1,3-dioxane-4-acetate.

200 MHz NMR (CDCl$_3$) $\delta$1.36 (m, 1H), 1.42 (s, 3H), 1.49 (s, 9H), 1.50 (s, 3H), 1.79 (dt, 1H, J=2.5 Hz, J=12.1 Hz), 2.40 (dd, 1H, J=6.2 Hz, J=15.4 Hz), 2.5–2.7 (m, 1H), 2.55 (d, 2H, J=6.1 Hz) 4.18 (m, 1H), 4.32 (m, 1H).

$^{13}$C-NMR (CDCl$_3$, 50 MHz) $\delta$19.80, 25.16, 28.30, 29.94, 35.66, 42.56, 65.27, 65.87, 80.96, 99.57, 116.72, 169.83.

GCMS m/e 254, 199, 198, 154, 138, 59, 57, 43, 41.

FTIR (neat) 954.2, 987.6, 1152.3, 1201.1, 1257.7, 1316.9, 1368.3, 1383.7, 1728.4, 2253.1, 2942.4, 2983.5 cm$^{-1}$.

Step B: Preparation of ($\pm$)-cis-1,1-dimethylethyl 6-(2-aminoethyl)-2,2-dimethyl-1,3-dioxane-b 4-acetate.

A solution of 6.75 g of ($\pm$)-cis-1,1-dimethyl ethyl 6-(cyanomethyl)-2,2-dimethyl-1,3-dioxane-4-acetate in 80 mL of methanol saturated with gaseous ammonia is treated with 0.7 g of Raney nickel #30 and hydrogen gas in a shaker at 50 pounds per square inch gage (psig) and 40° C. After 10 hours, thin layer chromatography indicates no starting nitrile present. The suspension is cooled, filtered through filter aid, and concentrated to an oil. This crude oil is purified by flash chromatography on silica gel with 30:20:1 (ethyl acetate:methanol-ammonium hydroxide) as eluent to give 5.48 g of ($\pm$)-cis-1,1-dimethylethyl 6-(2-aminoethyl)-2,2-dimethyl-1,3-dioxane-4-acetate (98.2 area %) as a clear oil which hardens after time.

200 MHz NMR (CDCl$_3$) $\delta$1.0–1.2 (m, 1H), 1.22 (s, 3H), 1.31 (s, 12H), 1.35–1.45 (m, 1H), 1.77 (brS, 2H), 2.15 (dd, 1H, J=15.1 Hz, J=6.2 Hz), 2.29 (dd, 1H, J=15.1 Hz, J=7.0 Hz), 2.66 (t, 2H, J=6.6 Hz), 3.82 (m, 1H), 4.12 (m, 1H).

$^{13}$C-NMR (CDCl$_3$, 50 MHz) $\delta$19.56, 27.92, 29.96, 36.43, 38.18, 39.65, 42.55, 66.03, 67.16, 80.19, 98.32, 169.80.

GC/MS m/e 258, 216, 215, 202, 200, 142, 113, 100, 99, 72, 57, 43.

FTIR (neat) 951.6, 1157.4, 1201.1, 1260.3, 1314.3, 1368.3, 1381.2, 1728.4, 2361.1, 2939.8, 2980.9 cm$^{-1}$.

Step C: Preparation of Trans-($\pm$)-5-(4-fluorophenyl)-2-(1-methylethyl)-N,4-diphenyl-1-[2-(tetrahydro-4-hydroxy-6-oxo-2H-pyran-2-yl)ethyl]-1H-pyrrole-3-carboxamide.

A solution of 0.79 g (2.89 mmol) of ($\pm$)-cis-1,1-dimethylethyl 6-(2-aminoethyl)-2,2-dimethyl-1,3-dioxane-4-acetate and 1.00 g (2.41 mmol) of ($\pm$)-4-fluoro-$\alpha$-[2-methyl-1-oxopropyl]-$\gamma$-oxo-N,$\beta$-diphenylbenzenebutaneamide mixture of [R-(R*,R*)], [R-(R*,S*)], [S-(R*,R*)] and [S-(R*,S*)] isomers in 15 mL of heptane:toluene (9:1) is heated at reflux for 24 hours. The solution is cooled and poured into 100 mL of tetrahydrofuran and 50 mL of saturated ammonium chloride in water. The layers are separated and the organic layer washed with brine. To the organic layer is added 5 mL of 10% hydrochloric acid solution and the solution is stirred for 15 hours. To this solution is added 1.2 g of sodium hydroxide and the mixture is stirred for 30 hours. The reaction is stopped by adding 50 mL of water, 30 mL of hexane, and separating the layers. The aqueous layer is acidified with dilute hydrochloric acid solution, stirred for three hours and extracted with 50 mL of ethyl acetate. A drop of concentrated hydrochloric acid is added to the ethyl acetate solution and the solution is allowed to stand 18 hours. The solution is concentrated in vacuo and the concentrate is redissolved in 50 mL of ethyl acetate and treated with one drop of concentrated hydrochloric acid. The solution is stirred two hours, concentrated in vacuo, and dissolved in 10 mL of toluene. Trans-($\pm$)-5-(4-fluorophenyl)-2-(1-methylethyl)-N,4-diphenyl-1-[2-(tetrahydro-4-hydroxy-6-oxo-2H-pyran-2-yl)ethyl]-1H-pyrrole-3-carboxamide is isolated in two crops.

METHOD I

Step A: Preparation of either ($\pm$)-(2$\alpha$,4$\alpha$,6$\alpha$) or ($\pm$)-(2$\alpha$,4$\beta$,6$\beta$)-1,1-dimethylethyl 6-(2-cyanomethyl)-2-phenyl-1,3-dioxane-4-acetate.

Either ($\pm$)-(2$\alpha$,4$\alpha$,6$\alpha$) or ($\pm$)-(2$\alpha$,4$\beta$,6$\beta$)-6-(cyanomethyl)-2-phenyl-1,3-dioxane-4-acetic acid (3.07 g, 11.75 mmol) is dissolved in 15 mL of dichloromethane, cooled to 0° C. and 0.1 g of 4-dimethylaminopyridine (DMAP) added, followed by t-butyl alcohol, followed by 2.91 g of dicyclohexylcarbodiimide (DCC). This solution is allowed to slowly warm to room temperature and stirred over a 16.5-hour period. Thin layer chromatography (TLC) shows mainly product, and some slightly lower Rf by-products. The mixture is stirred one hour and 50 mL of dichloromethane is added, and stirring is continued for five hours. An additional 100 mL of diethyl ether is added and then filtered. The precipitate is washed with diethyl ether. The filtrate is concentrated to an oil. The crude product is chromatographed on silica gel eluting with 4:1 hexane:ethyl acetate. The eluate is concentrated to yield either (±)-(2α,4α,6α) or (±)-(2α,4β,6β)-1,1-dimethylethyl 6-(2-cyanomethyl)-2-phenyl-1,3-dioxane-4-acetate.

GC/MS m/e 260, 244, 202, 138, 107, 105, 77, 57, 41.

Step B: Preparation of either (±)-(2α,4α,6α) or (±)-(2α,4β,6β) 1,1-dimethylethyl 6-(2-aminoethyl)-2-phenyl-1,3-dioxane-4-acetate.

A solution of 1.72 g of either (±)-(2α,4α,6α) or (±)-(2α,4β,6β)-1,1-dimethylethyl 6-(cyanomethyl)-2-phenyl-1,3-dioxane-4-acetate in 30 mL of methanol saturated with gaseous ammonia is treated with 0.3 g of Raney nickel #30 and hydrogen gas in a shaker at 50 pounds per square inch gage (psig) and 40° C. After 10 hours, thin layer chromatography indicates no starting nitrile present. The suspension is cooled, filtered through filter aid, and concentrated to an oil. This crude oil is purified by flash chromatography on silica gel with 30:20:1 (ethyl acetate:methanol:ammonium hydroxide) as eluent to give 1.56 g of either (±)-(2α,4α,6α) or (±)-(2α,4β,6β)-1,1-dimethylethyl 6-(2-aminoethyl)-2-phenyl-1,3-dioxane-4-acetate (98.2 area %) as a clear oil which hardens after time.

200 MHz NMR (CDCl$_3$) δ1.2–1.9 (m, 4H), 1.44 (s, 9H), 2.03, (br.s, 2H), 2.42 (dd, 1H, J=15.3 Hz, J=6.3 Hz), 2.63 (dd, 1H, J=15.3 Hz, J=7.0 Hz), 2.89 (t, 2H, J=6.8 Hz), 3.97 (m, 1H), 4.26 (m, 1H), 5.56 (s, 1H), 7.3–7.4 (m, 3H), 7.4–7.5 (m, 2H).

$^{13}$C NMR (CDCl$_3$, 50 MHz) δ28.07, 36.57, 38.23, 39.25, 42.17, 73.47, 74.87, 80.60, 100.36, 125.82, 127.88, 128.34, 138.45, 169.73.

GC/MS, m/e 321, 320, 248, 215, 174, 142, 105, 57.

FTIR (film) 699.6, 756.2, 1026.2, 1116.2, 1149.7, 1368.3, 1394.0, 1718.1, 1733.5, 2872.9, 2932.1 cm$^{-1}$.

Step C: Preparation of Trans-(±)-5-(4-fluorophenyl)-2-(1-methylethyl)-N,4-diphenyl-1-[2-(tetrahydro-4-hydroxy-6-oxo-2H-pyran-2-yl)ethyl]-1H-pyrrole-3-carboxamide.

In a process analogous to Method H by substituting (±)-(2α,4α,6α) or (±)-(2α,4β,6β) 1,1-dimethylethyl-6-(2-aminoethyl)-2-phenyl-1,3-dioxane-4-acetate for (±)-cis-1,1-dimethylethyl 6-(2-aminoethyl)-2,2-dimethyl-1,3-dioxane-4-acetate one obtains the title compound.

METHOD J

Step A: Preparation of (±)-cis-1,1-dimethylethyl 4-(cyanomethyl)-1,5-dioxaspiro[5.5]undecane-2-acetate.

(±)-cis-4-(cyanomethyl)-1,5-dioxaspiro[5.5]undecane-2-acetic acid 3.32 g (13.12 mmol), is dissolved in 15 mL of dichloromethane, cooled to 0° C. and 0.1 g of 4-dimethylaminopyridine (DMAP) added, followed by t-butyl alcohol, and followed by 3.25 g of dicyclohexylcarbodiimide (DCC). This solution is stirred and allowed to slowly warm to room temperature over a 16.5-hour period. TLC shows mainly product, and some slightly lower Rf by-product. The mixture is stirred one hour and 50 mL of dichloromethane is added and stirring continued four hours. One hundred mL of diethyl ether is added and then filtered. The filtrate is concentrated at reduced pressure. This crude concentrate is chromatographed on silica gel and eluted with 4:1 hexane:ethyl acetate to yield (±)-cis-1,1-dimethylethyl 4-(cyanomethyl)-1,5-dioxaspiro[5.5]undecane-2-acetate.

200 MHz NMR (CDCl$_3$) δ1.1–2.0 (m, 12H) 1.43 (s, 9H), 2.36 (m, 2H), 2.48 (m, 2H), 4.1–4.4 (m, 2H).

$^{13}$C-NMR (CDCl$_3$, 50 MHz) 22.37, 22.45, 25.08, 28.15, 28.55, 35.80, 38.57, 42.59, 64.31, 64.92, 80.76, 99.56, 116.65, 169.82.

GC/MS m/e 309 (m$^+$), 266, 224, 210, 138, 120, 99, 57, 55.

FTIR (KBr) 964.5, 1149.7, 1157.4, 1332.3, 1368.3, 1712.9, 2939.8 cm$^{-1}$.

Step B: Preparation of (±)-cis-1,1-dimethylethyl 4-(2-aminoethyl)-1,5-dioxaspiro[5.5]undecane-2-acetate.

A solution of 1.19 g of (±)-cis-1,1-dimethylethyl 4-(cyanomethyl)-1,5-dioxaspiro[5.5]undecane-2-acetate in 30 mL of methanol saturated with gaseous ammonia is treated with 0.3 g of Raney nickel #30 and hydrogen gas in a shaker at 50 pounds per square inch gage (psig) and 40° C. After 22 hours, thin layer chromatography indicates no starting nitrile present. The suspension is cooled, filtered through filter aid, and concentrated to an oil. This crude oil is purified by silica gel flash chromatography (30:20:1; ethyl acetate:methanol:ammonium hydroxide) to give 1.18 g of (±)-cis-1,1-dimethylethyl 4-(2-aminoethyl)- 1,5-dioxaspiro[5.5]undecane-2-acetate as a clear oil which solidifies upon standing.

200 MHz NMR (CDCl$_3$) δ1.2–2.0 (m, 12H), 1.43 (s, 9H), 2.34, (m, 2H), 2.50 (br.s, 2H), 2.84 (t, 2H, J=6.7 Hz), 3.99 (m, 1H), 4.28 (m, 1H).

GC/MS, m/e 313, 270, 214, 185, 144, 142, 99.

FTIR (film) 961.9, 1098.2, 1154.8, 1368.3, 1725.8, 2934.6 cm$^{-1}$.

Step C: Preparation of Trans-(±)-5-(4-fluorophenyl)-2-(1-methylethyl)-N,4-diphenyl-1-[2-(tetrahydro-4-hydroxy-6-oxo-2H-pyran-2-yl)ethyl]-1H-pyrrole-3-carboxamide.

In a process analogous to Method H by substituting (±)-cis-1,1-dimethylethyl 4-(2-aminoethyl)-1,5-dioxaspiro[5.5]undecane-2-acetate for (±)-cis-1,1-dimethylethyl 6-(2-aminoethyl)-2,2-dimethyl-1,3-dioxane-4-acetate one obtains the title compound.

EXAMPLE 3

(2R-Trans-5-(4-fluorophenyl)-2-(1-methylethyl)-N,4-diphenyl-1-[2-(tetrahydro-4-hydroxy-6-oxo-2H-pyran-2-yl)ethyl]-1H-pyrrole-3-carboxamide.

METHOD A

Step A: Preparation of (R)-1,1-dimethylethyl 6-cyano-5-[[(1,1-dimethylethyl)dimethylsilyl]oxy]-3-oxohexanoate.

(R)-4-cyano-3-[[(1,1-dimethylethyl)dimethylsilyl]oxy]butanoic acid, 32 g (0.132 mol), is dissolved in 300 mL of tetrahydrofuran. The solution is cooled to −20° C. and carbonyldiimidazole, 27 g (0.165 mol), is added. The solution is stirred and allowed to warm to 25° C. over two hours. The solution is added to a slurry of potassium 1,1-dimethylethyl malonate (half ester, half salt), 60 g (0.3 mol), anhydrous magnesium chloride, 27.2 g (0.246 mol), diisopropylethylamine, 53 mL (0.3 mol) in 700 mL of dry acetonitrile. The mixture is stirred at 5° C. for 18 hours and at 15° C. for 108 hours. The mixture is poured into a mixture of 1 L of 1N hydrochloric acid and 1 L of ethyl acetate and the resulting two-phase system is stirred for 15 minutes. The layers are separated. The organic layer is washed with 500 mL of saturated salt solution and concentrated to yield an oil. The oil consists of (R)-1,1-dimethylethyl 6-cyano-5-[[(1,1-dimethylethyl)dimethylsilyl]oxy]-3-oxohexanoate and some 1,1-dimethylethyl malonate (half ester, half acid) that is used directly in Step B. The oil has acceptable NMR spectra after subtracting the recovered malonate spectra.

Step B: Preparation of (R)-1,1-dimethylethyl 6-cyano-5-hydroxy-3-oxo-hexanoate.

A solution of crude (R)-1,1-dimethylethyl 6-cyano-5-[[(1,1-dimethylethyl)dimethylsilyl]oxy]-3-oxohexanoate, 43 g (0.126 mol) in 350 mL of tetrahydrofuran is treated with 213 mL of tetrabutylammonium fluoride solution (1.0M in hexane). The resulting mixture is stirred for five hours, at 25° C. The mixture is treated with 500 mL of water, 300 mL of diethyl ether is added, and the layers separated. The organic layer is dried (magnesium sulfate) and then filtered through a plug of silica gel with the aid of anhydrous diethyl ether. The solvent is removed under a vacuum to obtain 21 g of crude (R)-1,1-dimethylethyl 6-cyano-5-hydroxy-3-oxohexanoate with acceptable NMR, MS and IR spectra.

200 MHz NMR (CDCl$_3$) δ1.48 (s, 9H), 2.62 (m, 2H), 2.89 (d, 2H, J=6.1), 3.43 (s, 2H), 4.41 (pentet, 2H, J=6.1 Hz)

$^{13}$C-NMR (CDCl$_3$, 50 mHz) δ25.05, 27.86, 48.03, 50.81, 63.39, 82.43, 117.03, 165.84, 202.03.

MS (Chemical ionization) m/e 228, 200, 172, 154.

FTIR (KBr) 1144.5, 1327.2, 1370.9, 1715.5, 1733.5, 2253.1, 2934.6, 2980.9, 3459.3 cm$^{-1}$.

Step C: Preparation of [R-(R*,R*)]-1,1-dimethylethyl 6-cyano-3,5-dihydroxyhexanoate.

Crude (R)-1,1-dimethylethyl 6-cyano-5-hydroxy-3-oxohexanoate, 21 g (0.0924 mol), is dissolved in 940 mL of tetrahydrofuran and 190 mL of methanol under a nitrogen atmosphere. This solution is cooled to −85° C. and 95 mL of a 15% solution of methoxydiethylborane in tetrahydrofuran is added. The reaction is cooled to −97° C. and 6.5 g (0.172 mol) of sodium borohydride is added in 0.5 g portions over 1.5 hours. The reaction is maintained between −93° C. and −97° C. for 13 hours and allowed to warm to room temperature and stand for 60 hours under a nitrogen atmosphere. The reaction is quenched by the addition of 25 mL (0.395 mol) acetic acid and concentrated by vacuum distillation to an oil. The residue is dissolved with 500 mL methanol, concentrated by vacuum distillation, redissolved with 500 mL methanol and reconcentrated by vacuum distillation to give a dark brown oil. This oil is taken up in 500 mL of ethyl acetate and filtered through a plug of silica gel with the aid of 250 mL of ethyl acetate. The solution is evaporated to give 15 g of crude [R-(R*,R*)]-1,1-dimethylethyl 6-3,5-dihydroxyhexanoate which is used without further purification.

Step D: Preparation of (4R-cis)-1,1-dimethylethyl 6-cyanomethyl-2,2-dimethyl-1,3-dioxane-4-acetate.

Crude [R-(R*,R*)]-1,1-dimethylethyl 6-cyano-3,5-dihydroxyhexanoate, 15 g (61 mol), is dissolved in 150 mL of 2,2-dimethoxypropane, camphorsulfonic acid is added, and the solution is stirred for 18 hours at room temperature. Concentration and flash chromatography after concentration in vacuo provides 11.8 g of (4R-cis)-1,1-dimethyethyl 6-cyanomethyl-2,2-dimethyl-1,3-dioxane-4-acetate as an off-white solid, mp 64.7°-68° C. with acceptable IR, NMR, C-NMR and analysis.

200 MHz NMR (CDCl$_3$) δ1.36 (m, 1H), 1.42 (s, 3H), 1.49 (s, 9H), 1.50 (s, 3H), 1.79 (dt, 1H, J=2.5 Hz, J=12.1 Hz), 2.40 (dd, 1H, J=6.2 Hz, J=15.4 Hz), 2.5-2.7 (m, 1H), 2.55 (d, 2H, J=6.1 Hz), 4.18 (m, 1H), 4.32 (m, 1H).

$^{13}$C-NMR (CDCl$_3$, 50 MHz) δ19.74, 25.09, 28.24, 29.88, 35.58, 42.50, 65.20, 65.81, 80.87, 99.48, 116.68, 169.75.

GC/MS m/e 254, 198, 154, 138, 120, 59, 57, 43, 41.

FTIR (KBr) 941.4, 1116.2, 1154.8, 1188.3, 1257.7, 1293.7, 1309.1, 1368.3, 1725.8, 2361.1, 2983.5, 2996.4 cm$^{-1}$.

Step E: Preparation of (4R-cis)-1,1-dimethylethyl 6-(2-aminoethyl)-2,2-dimethyl-1,3-dioxane-4-acetate.

A solution of (4R-cis)-1,1-dimethylethyl 6-cyanomethyl-2,2-dimethyl-1,3-dioxane-4-acetate, 5.63 g (0.048 mol), in 100 mL of methanol saturated with gaseous ammonia is treated with 0.5 g of Raney nickel #30 and hydrogen gas in a shaker at 50 psi and 40° C. After 16 hours, thin layer chromatography indicates no starting nitrile present. The suspension is cooled, filtered through filter aid, and concentrated to an oil. This crude oil is purified by flash chromatography on silica gel with 30:20:1 (ethyl acetate:methanol:ammonium hydroxide) as eluent to give 4.93 g of of (4R-cis)-1,1-dimethyethyl 6-(2-aminoethyl)-2,2-dimethyl-1,3-dioxane-4-acetate (98.2 area %) as a clear oil with acceptable IR, NMR, C-NMR and MS spectra.

200 MHz NMR (CDCl$_3$) 1.0-1.2 (m, 1H), 1.22 (s, 3H), 1.31 (s, 12 H), 1.35-1.45 (m, 3H), 2.15 (dd, 1H, J=15.1 Hz, J=6.2 Hz), 2.29 (dd, 1H, J=15.1 Hz, J=7.0 Hz), 2.66 (t, 2H, J=6.6 Hz), 3.82 (m, 1H), 4.12 (m, 1H).

$^{13}$C-NMR (CDCl$_3$, 50 MHz) δ19.60, 27.96, 30.00, 36.50, 38.25, 39.79, 42.61, 66.08, 67.18, 80.21, 98.35, 169.82.

GC/MS m/e 202, 200, 173, 158, 142, 140, 114, 113, 100, 99, 97, 72, 57.

FTIR (neat) 951.6, 1159.9, 1201.1, 1260.3, 1314.3, 1368.3, 1381.2, 1731.0, 2870.3, 2939.8, 2980.9, 3382.2 cm$^{-1}$.

Step F: Preparation of (4R-cis)-1,1-dimethylethyl 6-[2[2-(4-fluorophenyl)-5-(1-methylethyl)-3-phenyl-4-[(phenylamino)carbonyl]-1H-pyrrol-1-yl]ethyl]-2,2-dimethyl-1,3-dioxane-4-acetate.

A solution of (4R-cis)-1,1-dimethylethyl 6-(2-aminoethyl)-2,2-dimethyl-1,3-dioxane-4-acetate, 1.36 g (4.97 mol), and (±)-4-fluoro-α-[2-methyl-1-oxopropyl]-γ-oxo-N,β-diphenylbenzenebutaneamide mixture of [R-(R*,R*)], [R-(R*,S*)], [S-(R*,R*)] and [S-R*,S*)] isomers, 1.60 g (3.83 mol), in 50 mL of heptane:toluene (9:1) is heated at reflux for 24 hours. The solution is cooled slightly and 15 mL of 2-propanol added. The mixture is allowed to cool to 25° C. and filtered to give 1.86 of (4R-cis)-1,1-dimethylethyl 6-[2[2-(4-fluorophenyl)-5-(1-methylethyl)-3-phenyl-4-[(phenylamino)carbonyl]-1H-pyrrol-1-yl]ethyl]-2,2-dimethyl-1,3-dioxane-4-acetate as a yellow solid with acceptable PNMR & C-NMR spectra.

¹H-NMR (CDCl₃, 200 MHz) δ1–1.7 (m, 5H), 1.30 (s, 3H), 1.36 (s, 3H), 1.43 (s, 9H), 1.53 (d, 6H, J=7.1 Hz), 2.23 (dd, 1H, J=15.3 Hz, J=6.3 Hz), 2.39 (dd, 1H, J=15.3 Hz, J=6.3 Hz), 3.5–3.9 (m, 3H), 4.0–4.2 (m, 2H), 6.8–7.3 (m, 14H).

¹³C-NMR (CDCl₃, 50 MHz) δ19.69, 21.60, 21.74, 26.12, 27.04, 28.12, 29.95, 36.05, 38.10, 40.89, 42.54, 65.92, 66.46, 80.59, 98.61, 115.00, 115.34, 115.42, 119.52, 121.78, 123.36, 126.44, 128.21, 128.31, 128.52, 128.75, 130.43, 133.01, 133.17, 134.69, 138.38, 141.47, 159.72, 164.64, 169.96.

Step G: Preparation of (2R-trans)-5-(4-fluorophenyl)-2-(1-methylethyl)-N,4-diphenyl-1-[2-(tetrahydro-4-hydroxy-6-oxo-2H-pyran-2-yl)ethyl]-1H-pyrrole-3-carboxamide.

(4R-cis)-1,1-dimethylethyl 6-[2[2-(4-fluorophenyl)-5-(1-methylethyl)-3-phenyl-4-[(phenylamino)carbonyl-1H-pyrrol-1-yl]ethyl]-2,2-dimethyl-1,3-dioxane-4-acetate, 4.37 g (6.68 mol), is dissolved in 200 mL of tetrahydrofuran and 15 mL of 10% hydrochloric acid solution is added, and the solution is stirred for 15 hours. To this solution is added sodium hydroxide (3.6 g) and the mixture is stirred for 30 hours. The reaction is stopped by adding 150 mL of water, 90 mL of hexane, and separating the layers. The aqueous layer is acidified with dilute hydrochloric acid solution, stirred for three hours and extracted with 150 mL of ethyl acetate. A drop of concentrated hydrochloric acid is added to the ethyl acetate solution and the solution is allowed to stand 18 hours. The solution is concentrated in vacuo and the concentrate is redissolved in 50 mL of ethyl acetate and treated with one drop of concentrated hydrochloric acid. The solution is stirred two hours, concentrated in vacuo, and dissolved in 3.0 mL of toluene. (2R-trans)-5-(4-fluorophenyl)-2-(1-methylethyl)-N,4-diphenyl-1-[2-(tetrahydro-4-hydroxy-6-oxo-2H-pyran-2-yl)ethyl]-1H-pyrrole-3-carboxamide (3.01 g) is isolated in two crops.

METHOD B

A solution of (4R-cis)-1,1-dimethylethyl 6-(2-aminoethyl)-2,2-dimethyl-1,3-dioxane-4-acetate, 2.56 g (9.36 mol), and (±)-4-fluoro-α-[2-methyl-1-oxopropyl]-γ-oxo-N,β-diphenylbenzenebutaneamide mixture of [R-(R*,R*)], [R-(R*,S*)], [S-(R*,R*)] and [S-(R*,S*)] isomers, 3.00 g (7.20 mol), in 60 mL of heptane:toluene (9:1) is heated at reflux for 24 hours. The solution is cooled and poured into 300 mL of tetrahydrofuran and 150 mL of saturated ammonium chloride in water. The layers are separated and the organic layer is added to 15 mL of 10% hydrochloric acid solution and the solution is stirred for 15 hours. To this solution is added sodium hydroxide (3.6 g) and the mixture is stirred for 30 hours. The reaction is stopped by adding 150 mL of water, 90 mL of hexane, and separating the layers. The aqueous layer is acidified with dilute hydrochloric acid solution, stirred for three hours and extracted with 150 mL of ethyl acetate. A drop of concentrated hydrochloric acid is added to the ethyl acetate solution and the solution is allowed to stand 18 hours. The solution is concentrated in vacuo and the concentrate is redissolved in 50 mL of ethyl acetate and treated with one drop of concentrated hydrochloric acid. The solution is stirred two hours, concentrated in vacuo, and dissolved in 3.0 mL of toluene. (2R-trans)-5-(4-fluorophenyl)-2-(1-methylethyl)-N,4-diphenyl-1-[2-(tetrahydro-4-hydroxy-6-oxo-2H-pyran-2-yl)-ethyl]1H-pyrrole-3-carboxamide (2.92 g) is isolated in two crops.

PREPARATION OF STARTING MATERIALS

EXAMPLE A 1-(4-Fluorophenyl)1,4-hexanedione.

A mixture of 36.61 g (295 mmol) of 4-fluorobenzaldehyde, 25 g (297.2 mmol) of ethyl vinyl ketone, 29 mL (206.9 mmol) of triethylamine and 11.94 g (44.25 mmol) of 3-benzyl-5-(2-hydroxyethyl)-4-methylthiazolium chloride is stirred and heated at 70° C. for six hours. The cooled solution is diluted with 2 liters of diethylether and washed with 2×300 mL of water, 2×100 mL of 2M hydrochloric acid, 100 mL of water, 200 mL of a saturated solution of sodium bicarbonate and brine. The organic layer is separated, dried (magnesium sulfate), filtered, and concentrated to provide 55 g of 1-(4-fluorophenyl)-1,4-hexanedione after recrystallization from methanol; mp 56°–57° C.

EXAMPLE B

4-Methyl-3-oxo-N-phenylpentanamide

A three-necked, 12-L round-bottom flask equipped with a mechanical stirrer, a thermometer and set up for distillation is charged with 2.6 L of toluene, 1.73 kg (12 mol) of methyl 4-methyl-3-oxopentanoate and 72 g (1.18 mol) of ethylene diamine. The mixture is heated to 80° C. and charged with 0.49 kg of aniline. The mixture is brought to reflux and distillation started. After 40 minutes a further 0.245 kg of aniline is charged and at 40 minute intervals a further two portions of aniline (0.245 and 2.5 kg) are charged. Distillation is continued for a further one to five hours until a total of 985 mL of solvent is removed. The solution is stirred at room temperature for 16 hours and a further 550 mL of solvent is removed by vacuum distillation (using approximately 85 mm Hg). The mixture is cooled and 2 L of water is charged to provide an oil. The mixture is warmed to 40° C. and a further 1.0 L of water is charged. Seven hundred milliliters of toluene-water mixture is removed by vacuum distillation (approximately 20 mm Hg). Two liters of water is charged and the mixture is allowed to stand for 10 days. The product is isolated by filtration and washed with three portions of hexane. Drying in vacuo gives 1.7 kg of 4-methyl-3-oxo-N-phenylpentanamide as a hydrate; mp 46.5°–58.8° C.

HPLC: 98.8%—retention time 3.56 min. 65/35 acetonitrile/water on a dry basis.

VPC: 87.6%—retention time 12.43 min. also 10.8% aniline (decomposition).

We claim:

1. A compound of Formula V

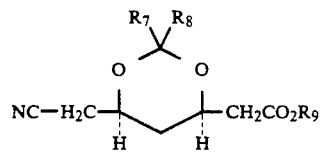

wherein R₇ and R₈ are independently hydrogen, alkyl of from one to three carbon atoms, phenyl or R₇ and R₈ are taken together as —(CH₂)ₙ—, wherein n is 4 or 5, and R₉ is alkyl of from one to eight carbon atoms, a three- to six-membered cycloalkyl group, or α,α-dimethylbenzyl.

2. A compound according to claim 1 wherein R₇ and R₈ are methyl, and R₉ is isopropyl.

3. A compound according to claim 1 wherein $R_7$ and $R_8$ are methyl, $R_9$ is tertiary butyl, and the two optically active centers are R.

4. A compound of Formula VI

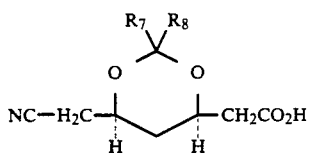   VI wherein $R^7$ and $R^8$ are independently hydrogen, alkyl of from one to three carbon atoms, phenyl or $R_7$ and $R_8$ are taken together as —$(CH_2)_n$—, wherein n is 4 or 5.

5. A compound according to claim 4 wherein $R_7$ and $R_8$ are methyl and the two optically active centers are R.

6. A compound of Formula VII

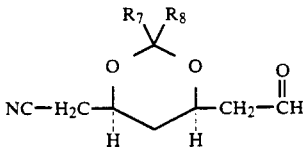   VII wherein $R_7$ and $R_8$ are independently hydrogen, alkyl of from one to three carbon atoms, phenyl or $R_7$ and $R_8$ are taken together as —$(CH_2)_n$—, wherein n is 4 or 5.

7. A compound according to claim 6 wherein $R_7$ and $R_8$ are methyl and the two optically active centers are R.

8. A compound of Formula VIII

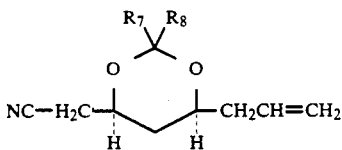   VIII wherein $R_7$ and $R_8$ are independently hydrogen, alkyl of from one to three carbon atoms, phenyl or $R_7$ and $R_8$ are taken together as —$(CH_2)_n$—, wherein n is 4 or 5.

9. A compound according to claim 8 wherein $R_7$ and $R_8$ are methyl and the two optically active centers are R.

* * * * *